(12) United States Patent
Kikuiri

(10) Patent No.: US 7,569,183 B2
(45) Date of Patent: Aug. 4, 2009

(54) FECAL ASSAY METHOD AND ANALYZER

(75) Inventor: Hideki Kikuiri, Tsuyama (JP)

(73) Assignee: Alfresa Pharma Corporation (JP)

( * ) Notice: Subject to any disclaimer, the term of this patent is extended or adjusted under 35 U.S.C. 154(b) by 773 days.

(21) Appl. No.: 11/093,065

(22) Filed: Mar. 28, 2005

(65) Prior Publication Data

US 2006/0216830 A1    Sep. 28, 2006

(51) Int. Cl.
*G01N 33/00* (2006.01)
(52) U.S. Cl. .............. 422/55; 422/50; 422/52; 422/58; 422/68.1; 422/82.05; 422/82.09; 422/99; 422/100; 422/102
(58) Field of Classification Search ........... 422/50, 422/52, 55, 58, 68.1, 82.05, 82.09, 99, 100, 422/102
See application file for complete search history.

(56) References Cited

U.S. PATENT DOCUMENTS 5,827,675 A * 10/1998 Skiffington et al. ............ 435/8

FOREIGN PATENT DOCUMENTS

| JP | 10-160728 | 6/1998 |
|----|-----------|--------|
| JP | 10-257881 | 9/1998 |
| JP | 11-64331 | 3/1999 |
| JP | 2000-258308 | 9/2000 |
| JP | 2001-183362 | 7/2001 |

* cited by examiner

*Primary Examiner*—Sam P Siefke
(74) *Attorney, Agent, or Firm*—Gerald E. Hespos; Anthony J. Casella

(57) ABSTRACT

A fecal analyzing apparatus includes an extraction/dilution section (43) for extracting a fecal suspension from a feces sampling container (1). The fecal suspension is formed by dispersing feces in a feces-dissolving liquid in the feces sampling container (1), and mixing a diluting solution having a different concentration than the feces-dissolving liquid, with respect to a specific pigment, into the extracted fecal suspension in a predetermined amount. An optical-absorbance measurement section (61) detects the concentration of the specific pigment to be changed in response to the addition of the diluting solution, and a control device (66) determines the adequacy of the extraction amount of the fecal suspension in accordance with the detected concentration of the specific pigment. The adequacy of the extraction amount of the fecal suspension can be determined to provide an adequate assay result.

7 Claims, 15 Drawing Sheets

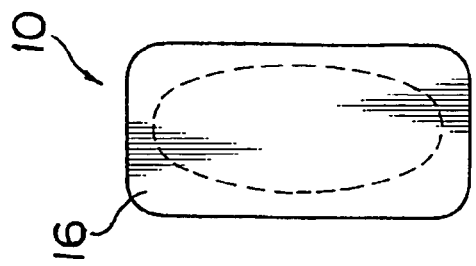
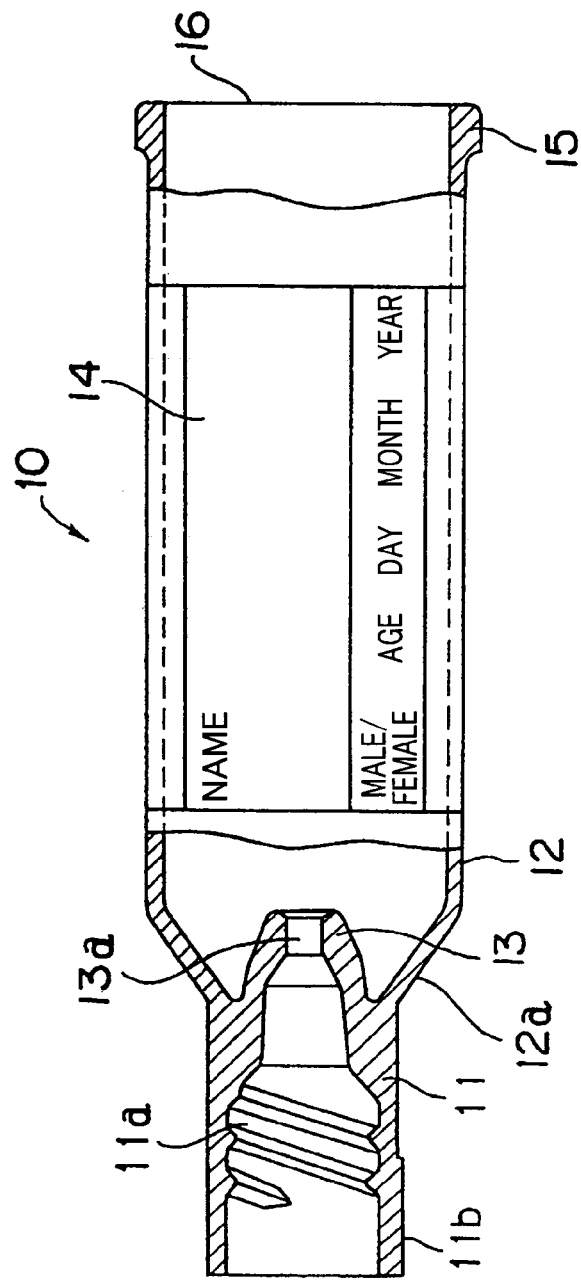

FIG.11

| | EXTRACTED FECAL SUSPENSION | ADDED DILUTING SOLUTION | MEASURED DIFFERENCE IN ABSORBANCE | REFERENCE DIFFERENCE IN ABSORBANCE | DETERMINATION RESULT $0.9a \leqq b \leqq 1.1a$ |
|---|---|---|---|---|---|
| DATA 1 | 10 μL | 100 μL | 0.116 | 0.111 | ○ |
| DATA 2 | 0 μL | | 0.000 | | × |
| DATA 3 | 5 μL | | 0.060 | | × |

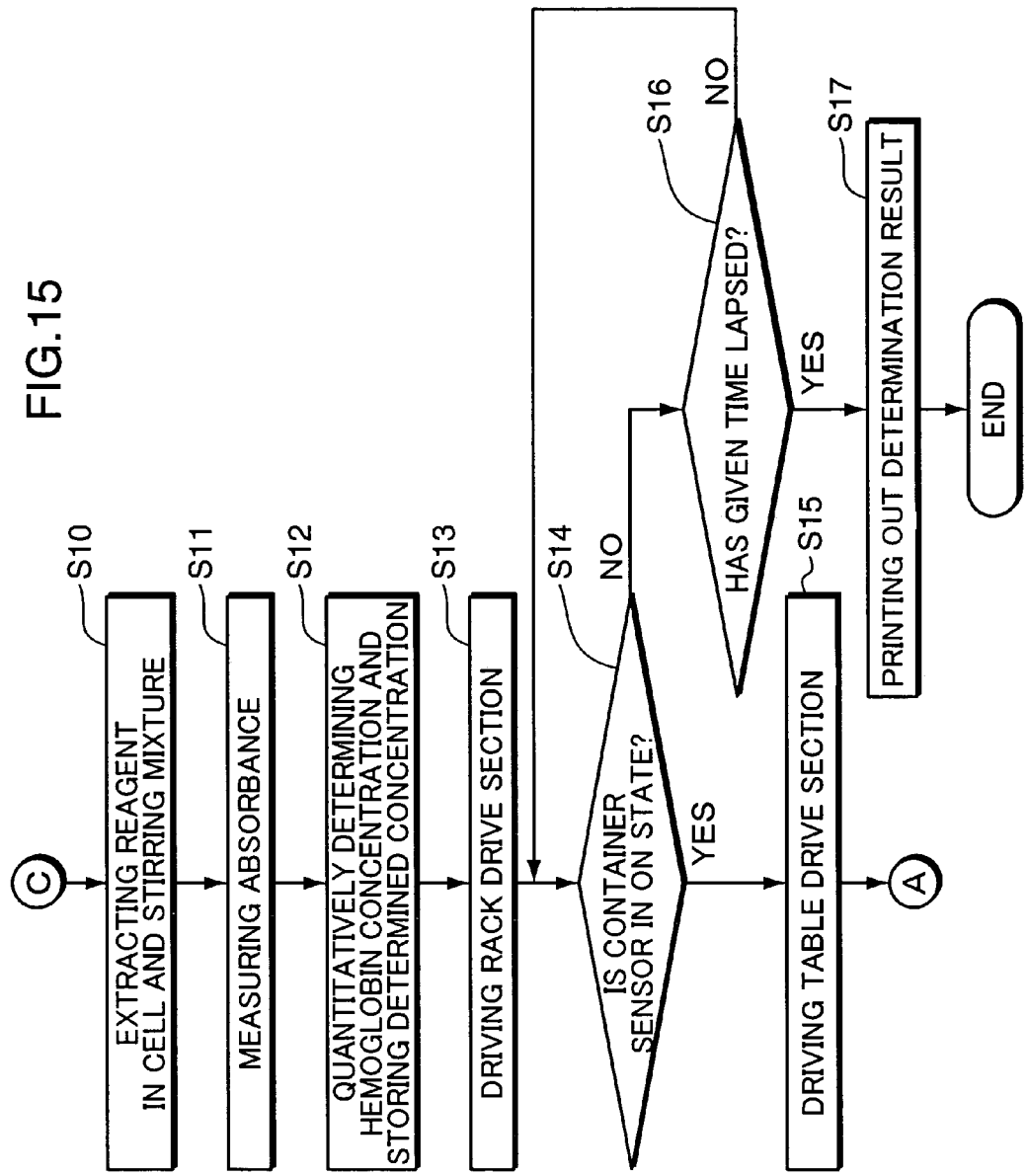

FECAL ASSAY METHOD AND ANALYZER

BACKGROUND OF THE INVENTION

1. Field of the Invention

The present invention relates to a feces sampling container for use in assaying feces as a specimen, and a method and analyzer for assaying feces.

2. Description of the Background Art

Heretofore, there has been known a feces sampling container, or a container for sampling feces as a specimen, as disclosed, for example, in the following Patent Publications 1 to 4:

[Patent Publication 1] Japanese Patent Laid-Open Publication No. 10-257881;

[Patent Publication 2] Japanese Patent Laid-Open Publication No. 2001-183362;

[Patent Publication 3] Japanese Patent Laid-Open Publication No. 10-160728; and

[Patent Publication 4] Japanese Patent Laid-Open Publication No. 2000-258308.

This type of feces sampling container comprises a feces sampling instrument, and a container body containing a feces-dissolving liquid, wherein the feces sampling instrument with feces attached thereon is immersed in the feces-dissolving liquid so as to disperse the feces over the feces-dissolving liquid to form a suspension. In a quantitative analysis of a component (e.g. hemoglobin) of feces using this type of feces sampling container, a certain amount of the suspension in the container body is extracted by a nozzle of an automatic analyzer from the upper side of the container body in a suction manner, and the extracted suspension is analyzed after diluted.

However, when the above quantitative analysis is performed using the conventional feces sampling containers as disclosed in Patent Publications 1 to 4, the automatic analyzer fails to extract an intended amount of the suspension in some cases.

For example, one factor of the failure is associated with the need for re-assay of the suspension. Specifically, in the above automatic analyzer, a particular result of the analysis may require a re-assay for the same suspension. In this case, the liquid level of the suspension in the feces sampling container will be inevitably lowered every time the re-assay is repeated. Thus, when the liquid level of the suspension is lowered beyond the position of a suction port of the nozzle due to repetition of the re-assay, the nozzle becomes unable to suck the suspension, which leads to deficiency in extraction amount of the suspension, or no extraction of the suspension in the worst case.

Another factor of the failure is associated with clogging of the nozzle of the above automatic analyzer. Specifically, the automatic analyzer is designed to introduce the nozzle into the suspension, and extract the suspension in a suction manner. Thus, if a relatively large agglomeration of feces or insoluble substance is contained in the suspension, the nozzle can be clogged therewith to hinder sucking the suspension in an intended amount.

While Patent Publications 3 and 4 disclose a container body which further includes a filter for filtering the suspension, and contains the filter in such a manner as to allow the suspension passing through the filter to be sucked by the nozzle, even this container cannot avoid the problems about deficiency in extraction amount of the suspension due to repetition of the re-assay.

The above built-in filter type container is designed to dispose the filter in such a manner as to be in contact with the feces-dissolving liquid in advance, and to assay the filtered suspension. This involves a risk that the concentration of an analyte in the filtered suspension is lowered by the feces-dissolving liquid pre-infiltrated in the filter.

In the conventional feces sampling container, if an intended amount of the suspension cannot be extracted from the feces sampling container for the above reasons, the extracted suspension will be directly diluted and without any recognition of the above fact, and the diluted suspension having a undesirable lowered concentration will be assayed, which is likely to result in a wrong assay result.

SUMMARY OF THE INVENTION

It is an object of the present invention to provide feces sampling and assay technology which has overcome the problems residing in the prior art.

It is another object of the present invention to provide a feces sampling container and a fecal assay method and analyzer which can determine excess and deficiency in extraction amount of a fecal suspension to obtain an adequate assay result.

According to an aspect of the invention, a feces sampling container contains a feces-dissolving liquid in such a manner as to be extracted by an analyzer. The feces-dissolving liquid is colored a different color from that of a diluting solution to be added into a fecal suspension formed by dispersing feces in the feces-dissolving liquid and extracted by the analyzer. The fecal suspension is extracted, and a diluting solution is added and mixed into/with the extracted fecal suspension in a predetermined amount. The concentration of the specific pigment to be changed is detected in response to the mixing of the diluting solution. The adequacy of the extraction amount of the fecal suspension is determined in accordance with the detected concentration of the specific pigment.

Other features and advantages of the present invention will be apparent from the accompanying drawings and from the detailed description.

BRIEF DESCRIPTION OF THE DRAWINGS

FIG. 1A is a partly sectional side view of a feces-dissolving-liquid receiver of a feces sampling container according to one embodiment of the present invention.

FIG. 1B is a bottom view of the receiver in FIG. 1A.

FIG. 11 is a comparative diagram of a reference optical absorbance and the difference between optical absorbance values measured by the analyzer in FIG. 6.

FIG. 15 is a flowchart showing a processing according to the control unit in FIG. 9.

DESCRIPTION OF THE PREFERRED EMBODIMENTS

With reference to the drawings, a preferred embodiment of the present invention will now be described.

Figure 2:
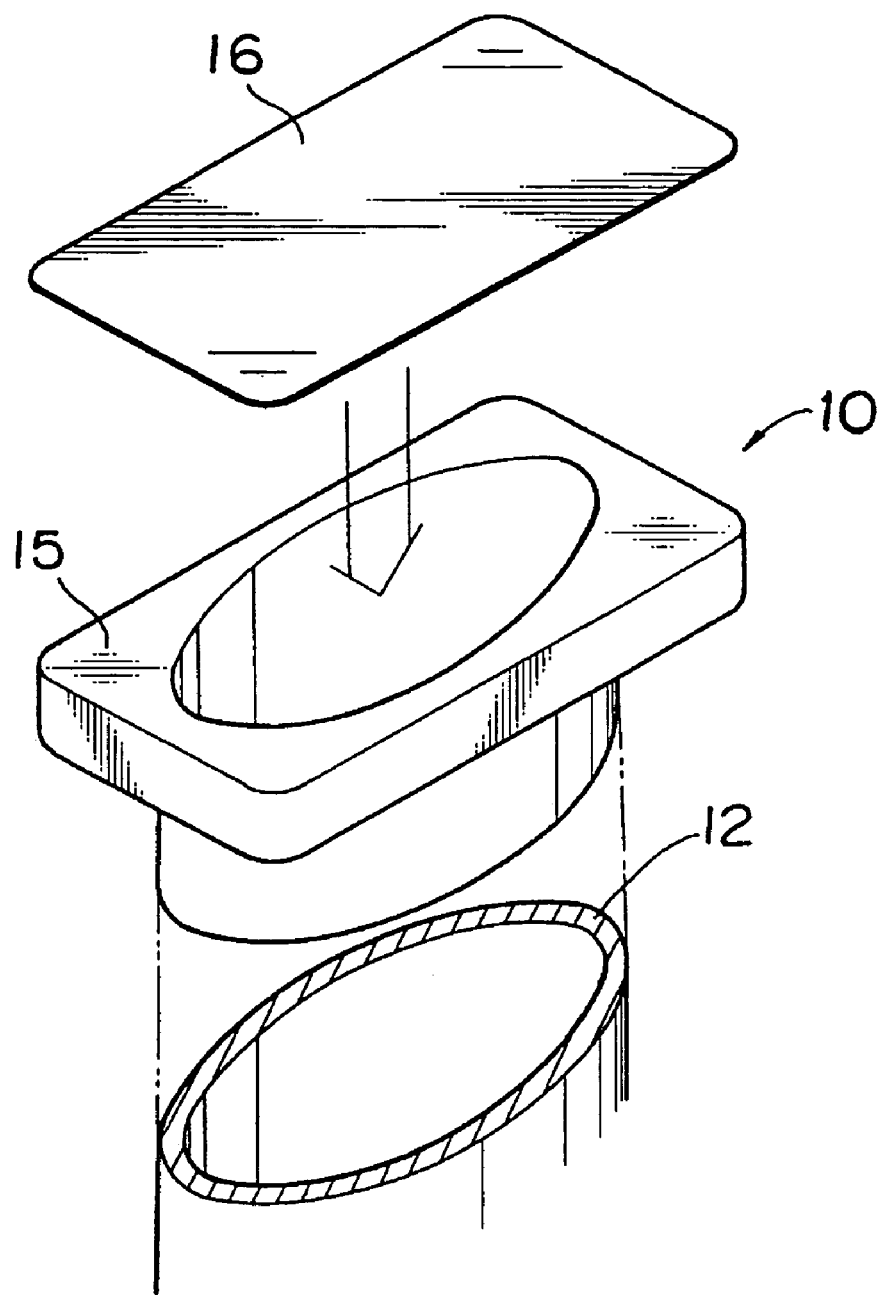
FIG. 2 is a perspective view showing a bottom structure of the receiver in FIG. 1A.
Figures 3A, 3B:
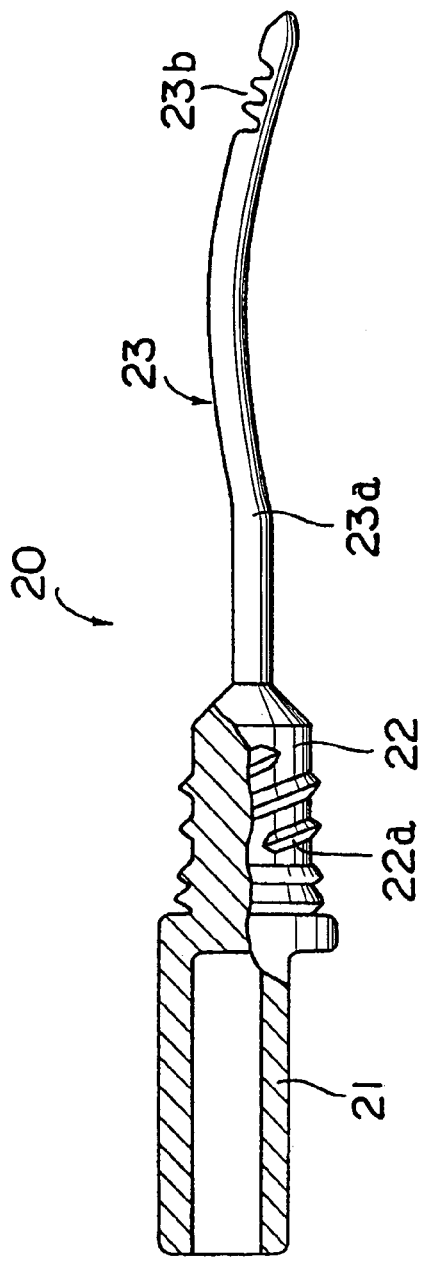
FIG. 3A is a front view of a specimen-sampling member of the feces sampling container according to the embodiment of the present invention.
FIG. 3B is a partly sectional side view of the specimen-sampling member in FIG. 3A.

A feces sampling container according to this embodiment comprises a fecal-dissolving-liquid receiver 10 illustrated in FIGS. 1 and 2, and a specimen-sampling member 20 illustrated in FIG. 3. The fecal-dissolving-liquid receiver 10, as will hereinafter be described in detail, contains a feces-dissolving liquid 17 for allowing feces to be dispersed thereover so as to form a fecal suspension 17a, as will hereinafter be described in detail, and the feces-dissolving liquid 17 is colored a different color from that of an after-mentioned diluting solution.

In one example, feces-dissolving liquid 17 may be prepared by adding 0.0123 mmol/L of BRILLIANT BLUE FCF (maximum absorption wavelength: 630 nm) to the following mixture:

| | |
|---|---|
| 30 mM | MES (2-Morpholinoethanesulfonic acid, monohydrate: pH 6.3) |
| 0.9% | sodium chloride |
| 0.2% | bovine serum albumin |
| 0.2% | boric acid |
| 1.8% | polyethylene glycol 20,000 |
| 0.1% | sodium azide |

The fecal-dissolving-liquid receiver 10 has a receiver body which is integrally formed as a single piece using a synthetic resin, and formed with an internal-thread portion 11 on the side of the top end thereof (on the left side on FIG. 1A). A portion of the fecal-dissolving-liquid receiver 10 on the side of the bottom portion thereof (on the right side on FIG. 1A) relative to the internal-thread portion 11 is formed as a feces-dissolving-liquid storage portion 12.

The internal-thread portion 11 has an approximately cylindrical shape, and an inner surface formed with an internal thread 11a. A top portion of the internal-thread portion 11 has an outer peripheral surface formed with a plurality of ribs 11b extending in the circumferential direction and in a direction from the top end to the rear end to facilitate a rotational operation to be performed by pinching this portion with user's fingers A scraping portion 13 extends from the internal-thread portion 11 toward the bottom portion to enter into the inner space of the feces-dissolving-liquid storage portion 12. The scraping portion 13 has a rear end formed as a scraping hole 13a with an inner diameter approximately equal to the outer diameter of an after-mentioned sampling bar 23 of the specimen-sampling member 20.

The feces-dissolving-liquid storage portion 12 has an oval-shaped cross-section as shown in FIG. 2, and a top-side portion of the feces-dissolving-liquid storage portion 12 is formed as a tapered portion 12a having a cross-sectional shape smoothly changing from the cross-sectional shape of the internal-thread portion 11 to the cross-sectional shape of the feces-dissolving-liquid storage portion 12. A label 14 is attached on the outer peripheral surface of the feces-dissolving-liquid storage portion 12. A user may write a subject's name and other on the label 14.

The bottom portion of feces-dissolving-liquid storage portion 12 extends straight and has an open end, and the peripheral edge of this bottom opening is formed as a flange 15. This flange 15 protrudes in the radial direction of the receiver relative to the remaining portion to have an approximately rectangular shape in the illustrated embodiment. A sealing film 16 having approximately the same profile as that of the flange 15 is attached on the end surface of the flange 15 to close the bottom opening.

The sealing film 16 is a composite film which comprises a thin substrate made of metal, such as aluminum, or synthetic resin, a corrosion-protective coating layer made of polyethylene or the like and formed on each of the top and rear surfaces of the substrate, and a thermal-bonding coating layer made of synthetic-resin (fundamentally the same material as that of the receiver body) and formed on the rear-side corrosion-protective coating layer, which are integrally formed as a laminated structure. That is, this sealing film 16 is attached on the end surface of the flange 15 through a thermal bonding process.

In the present invention, the above coating layers are not essential, and the attaching means of the sealing film 16 may be any suitable bonding means, such as ultrasonic welding or adhesives, as well as thermal bonding.

The specimen-sampling bar 20 is integrally formed as a single piece using synthetic resin, as with the receiver body, and has a pinch portion 21, an external-thread portion 22 and a sampling bar 23 in this order as shown in FIG. 3. The external-thread portion 22 is formed with an external thread 22a engageable with the internal-thread portion 11 of the fecal-dissolving-liquid receiver 10. The sampling bar 23 has an even diameter. The sampling bar 23 has a curved portion 23a formed to curve obtusely at a position adjacent to the external-thread portion 22, and a distal end portion curving in a different direction from (in the illustrated embodiment, an opposite direction to) the curving direction of the curved portion 23a. The sampling bar 23 has a distal end formed with a plurality of specimen-sampling grooves 23b on the outer side of the curvature of the distal end portion.

Figure 4:
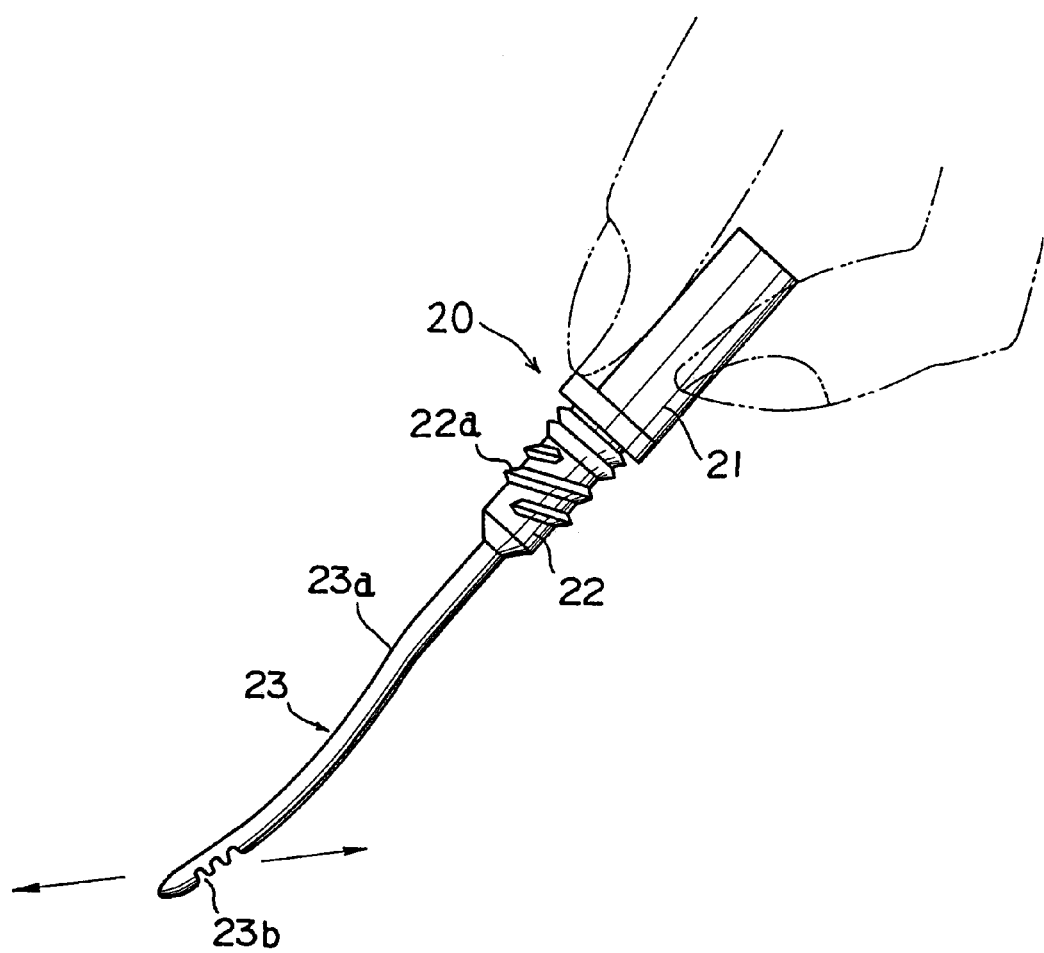
FIG. 4 is a schematic explanatory diagram of an operation for picking up a specimen using the specimen-sampling member in FIG. 3A.
Figure 5:
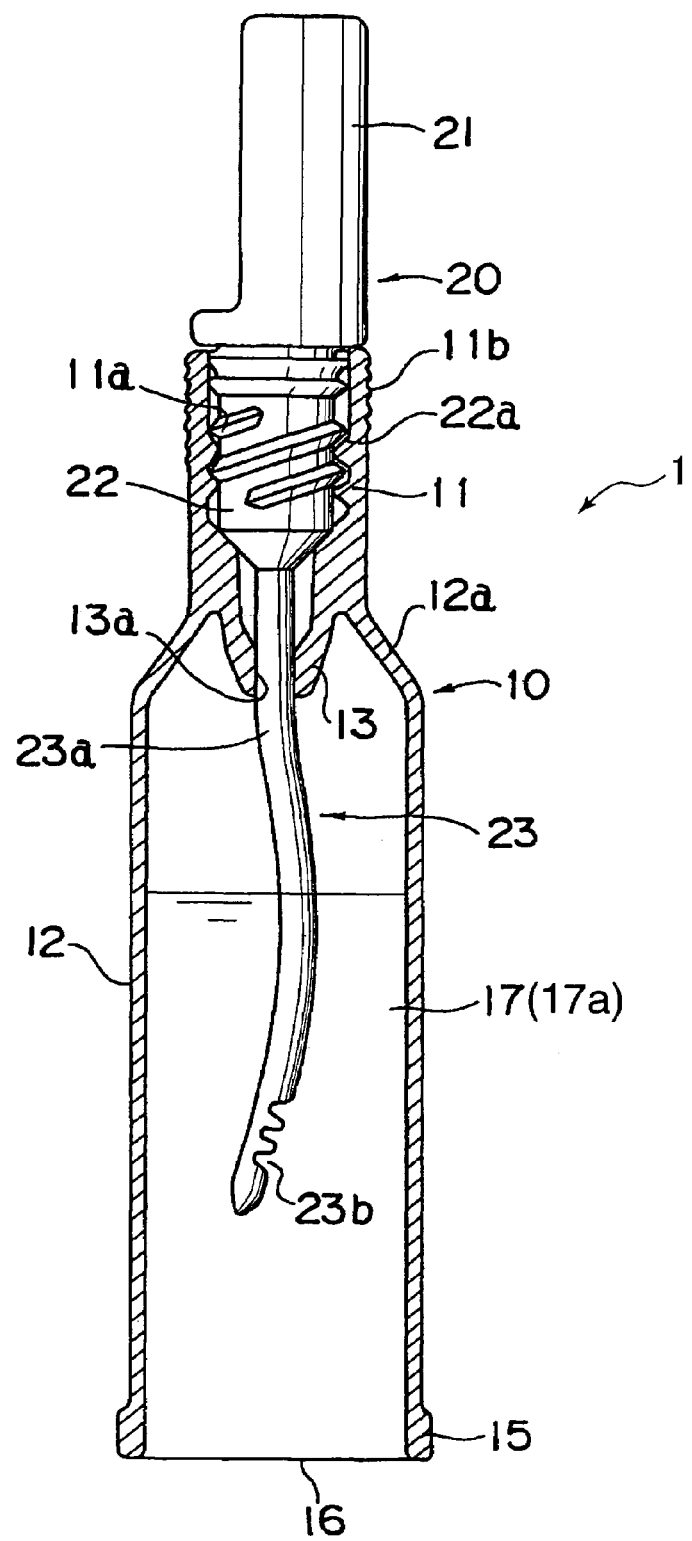
FIG. 5 is a sectional front view showing the state after the specimen-sampling member in FIG. 3A is attached to the feces-dissolving-liquid receiver in FIG. 1A.

With reference to FIGS. 4 and 5, a feces-sampling process using the above feces sampling container 1 will be described below.

As shown in FIG. 4, the distal end of the sampling bar 23 is scrapingly pressed onto feces as a specimen while pinching the pinch portion 21 of the specimen-sampling member 20 is pinched with fingers or the like, to allow the specimen to enter in the specimen-sampling grooves 23b at the distal end. During this operation, the curved center portion of the sampling bar 23 makes it possible to assure a sufficient distance between the specimen and the pinch portion 21 while allowing the distal end portion to get close to a horizontal posture, so as to prevent the specimen from attaching onto user's fingers or the like.

Then, as shown in FIG. 5, the top end of the fecal-dissolving-liquid receiver 10 containing the aforementioned feces-dissolving liquid 17 is positioned upward, and the distal end of the specimen-sampling member 20 is inserted into the fecal-dissolving-liquid receiver 10 from above (i.e. from the side of the external-thread portion 11), and then the specimen-sampling member 20 is rotated to bring the external-thread portion 22 into engagement with the internal-thread portion 11 so as to allow them to be in close contact with one another in this engagement portion. During this operation, when the distal end portion (i.e. the portion having the specimen attached thereon) of the sampling bar 23 passes through the scraping hole 13a of the scraping portion 13, an excessive part of the specimen on the sampling bar 23 is scraped off by the scraping portion 13, and thereby only an appropriate amount of the specimen getting into the specimen-sampling grooves 23b is immersed into the feces-dissolving liquid 17. The immersed specimen is dispersed in the feces-dissolving liquid 17 to form a fecal suspension 17a in the fecal-dissolving-liquid receiver 10.

Figure 6:
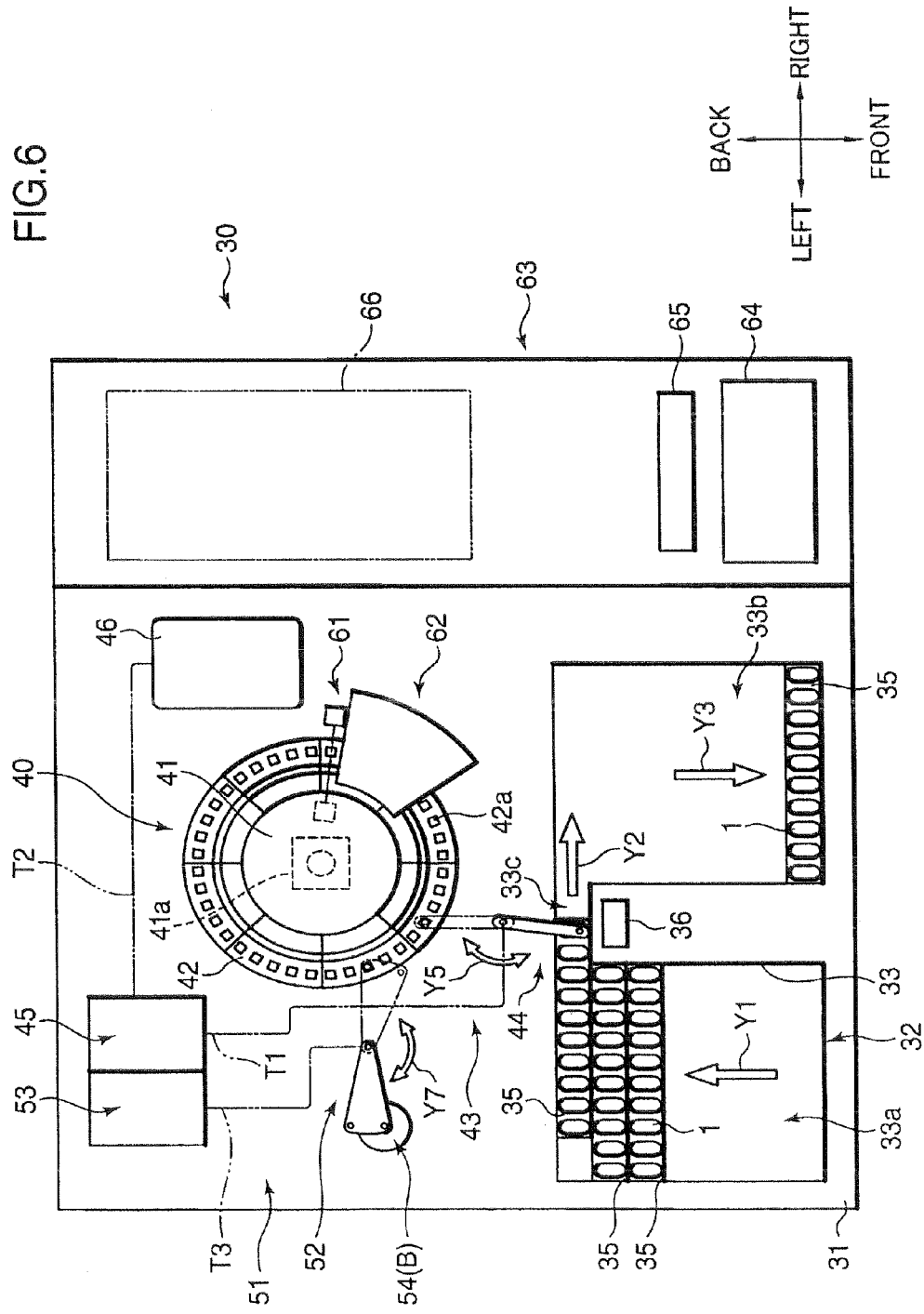
FIG. 6 is a top plan view of an analyzer according to one embodiment of the present invention.
Figure 7:
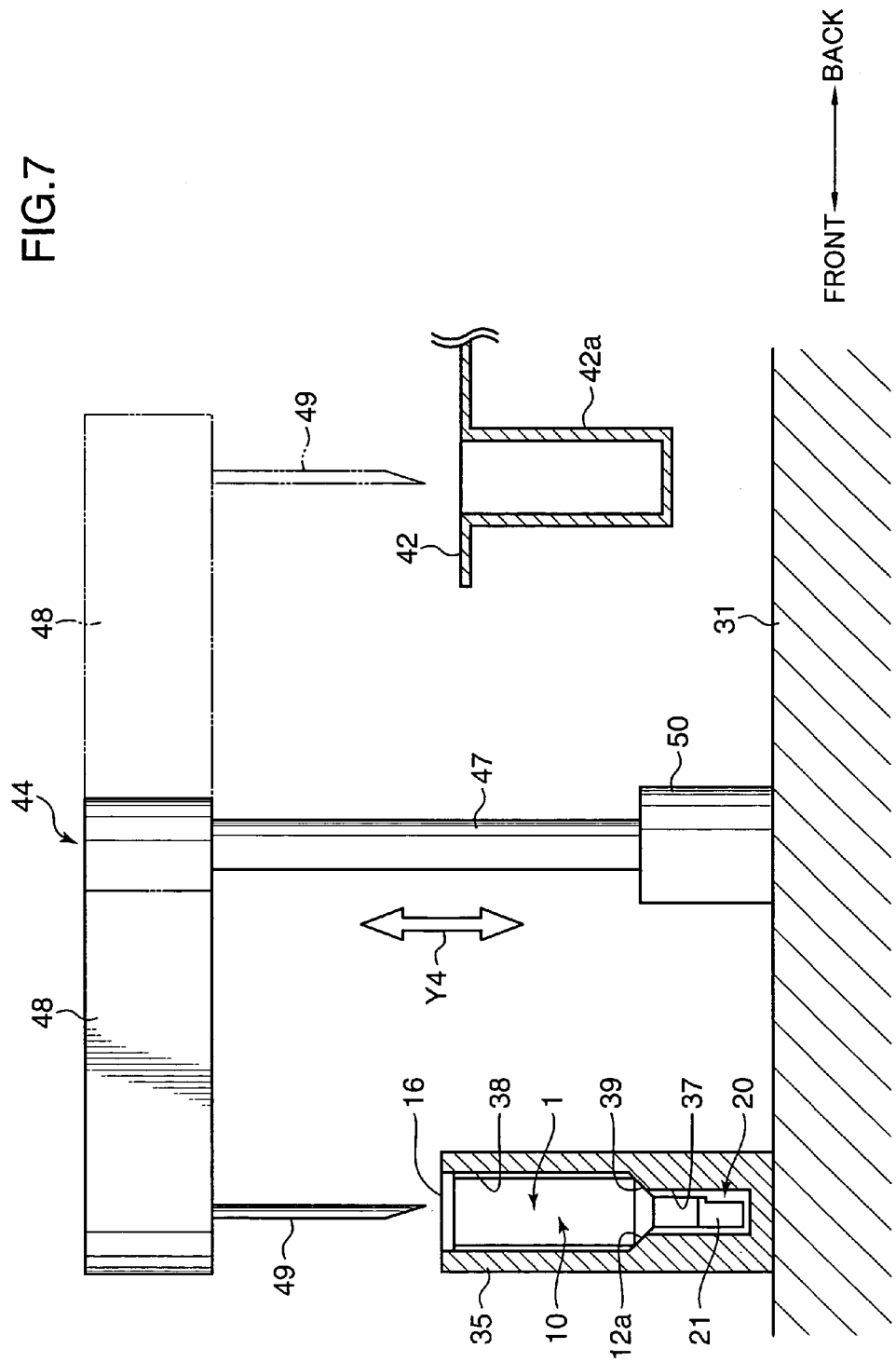
FIG. 7 is a partly sectional side view showing an extraction/dilution section of the analyzer in FIG. 6.
Figure 8:
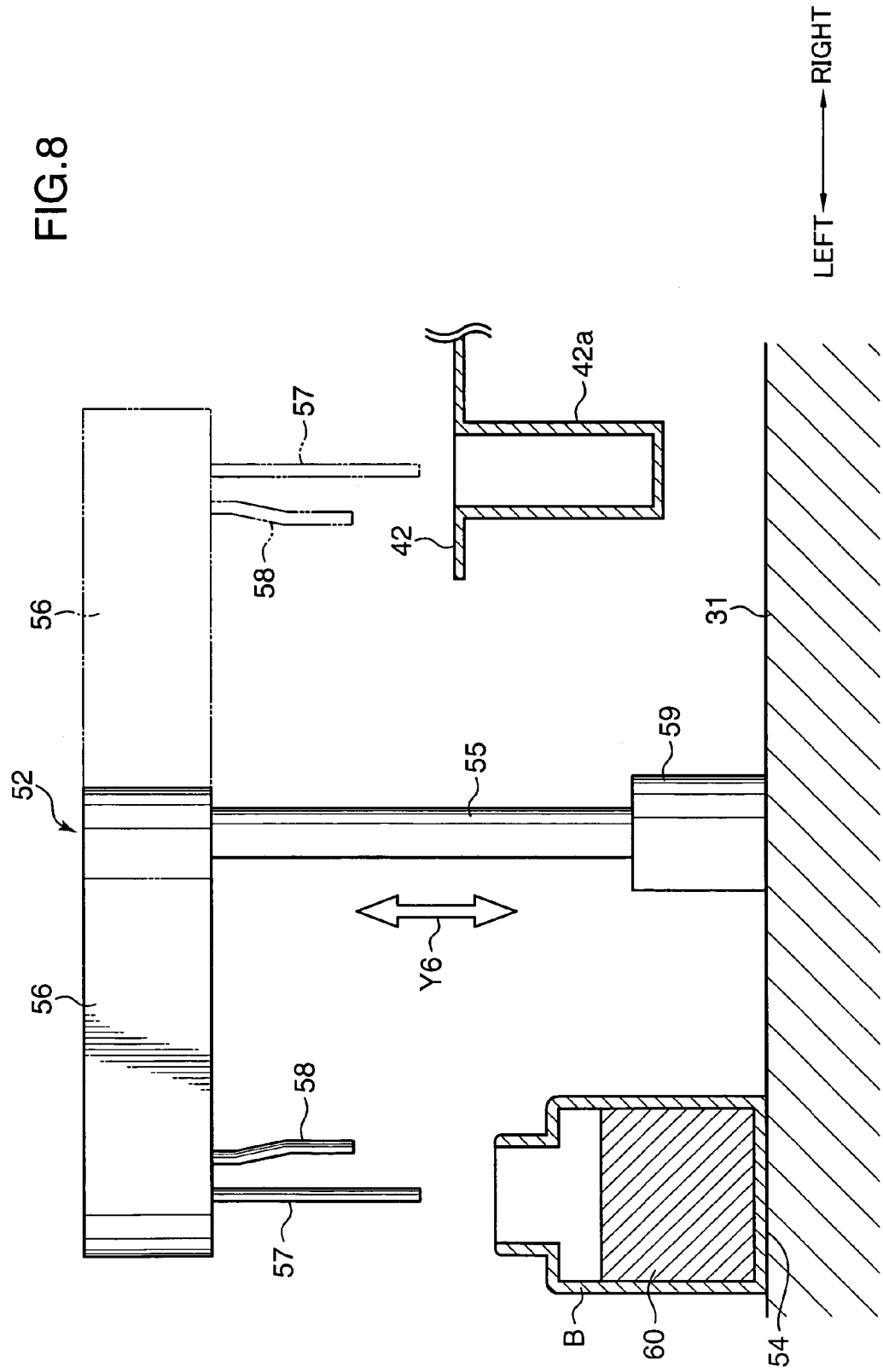
FIG. 8 is a partly sectional side view showing a reagent addition section of the analyzer in FIG. 6.

The feces sampling container 1 containing the fecal suspension 17a is directly transported to a medical facility or the like, and subjected to a quantitative analysis of a specific component included in the fecal suspension 17a. With reference to FIGS. 6 to 8, the structure of an analyzer will be described, by taking an analyzer for measuring a hemoglobin concentration in the fecal suspension 17a as an example.

As shown in FIG. 6, the analyzer 30 comprises a container holder 32 placed on a base 31 formed in an approximately oblong shape, a rotary table 40, an extraction/dilution section (extractor, diluter) 43, a reagent addition section (reagent adder) 51, an optical-absorbance measurement section (detector) 61, a cell cleaning section 62 and a control box 63. The following description will be made on the assumption that the position on the side of the container holder 32 is "front" or "frontward" in the width direction of the base 31, and the position on the side of the control box 63 is "right" or "rightward" in the longitudinal direction of the base 31.

The container holder 32 includes a receiving groove 33 having an opening facing upward relative to the base 31 to receive therein a plurality of after-mentioned container racks 35 each capable of holding the feces sampling container 1, and a rack drive section 34 (see FIG. 9) for transferring the container rack 35 along the receiving groove 33. The receiving groove 33 includes a set section 33a for allowing a user to place the container rack 35 thereon, a discharge section 33b disposed on the right side of the set section 33a to allow the container rack 35 holding an assayed feces sampling containers 1 to be discharged thereinto, and a connection section 33c connecting between the set section 33a and the discharge section 33b.

The rack drive section 34 is designed to transfer the container rack 35 in the set section 33a in the rearward direction as indicated by the arrow Y1, to transfer the container rack 35 located most rearward, toward the discharge section 33b (rightward) as indicated by the arrow Y2, and to transfer the container rack 35 in the discharge section 33b in the frontward direction as indicated by the arrow Y3. A container detection sensor 36 is disposed on the front side of the connection section 33c to detect specific-one or more of the feces sampling containers 1 held by the container rack 35 being transferred through the connection section 33c. The following description will be made on the assumption that the state when the container detection sensor 36 is detecting the feces sampling container 1 is "ON state".

As shown in FIGS. 6 and 7, the container rack 35 has a box-like shape having an upward opening, and can hold 10 of the feces sampling containers 1 in a line arrangement. More specifically, the container rack 35 has a small-diameter hole 37 far larger than the pinch portion 21 of the feces sampling container 1, a large-diameter hole 38 with a cross-sectional shape approximately equal to that of the flange 15, and a tapered portion 39 at the boundary between these holes. The feces sampling container 1 is inserted into the container rack 35 from the side of the pinch portion 21, and the tapered portion 12a of the feces sampling container 1 is placed on the tapered portion 39, so that the feces sampling container 1 can be held in a posture where the sealing film 16 or the bottom thereof is located at the uppermost position.

The rotary table 40 comprises a disc-shaped table body 41 disposed on the rearward side of the container holder 32, and a table drive section 41a including a motor disposed under the base 31. The table drive section 41a is operable to rotate the table body 41 relative to the base 31 around a vertical axis (axis of the table body 41). The table drive section 41a has a rotary encoder or the like to detect the rotational position of the table body 41 while rotating the table body 41. Eight cuvettes 42 are detachably provided along the peripheral edge of the table body 41. Each of the cuvettes 42 has five cells 42a arranged concentrically to the table body 41 in an arc shape. As shown in FIG. 7, each of the cells 42a has a cup-like shape having an upward opening. Further, in order to adequately perform an optical-absorbance measurement according to an after-mentioned optical-absorbance measurement section 61, the material and shape of the cell 42a are selected to have no optical absorption in a measurement wavelength range (e.g. material and shape equivalent to a conventional glass cell or quartz cell).

The extraction/dilution section 43 comprises a manipulation section 44 disposed between the container holder 32 and the rotary table 40, a pump section 45 in fluid communication with the manipulation section 44, and a diluting-solution vessel 46. As shown in FIGS. 6 and 7, the manipulation section 44 includes a support column 47 extends upward from the base 31, an arm 48 attached to the support column 47 in a cantilevered manner to extend in a direction orthogonal to the support column 47, a nozzle 49 attached to the end of the arm 48 to extend downward, and an arm drive section 50 operable to stretch and retract the support column 47 relative to the base 31 in a direction indicated by the arrow Y4 and rotate the support column 47 around its axis in a direction indicated by the arrow Y5. The pump portion 45 is designed to allow the nozzle 49 to suck the fecal suspension 17a in a predetermined amount, and internally provided with a syringe (not shown) capable of being stroke-controlled by a ball screw or the like to discharge a given amount of diluting solution from the nozzle 49. This syringe is in fluid communication with the nozzle 49 and the diluting-solution vessel 46, respectively, through connection tubes T1 and T2.

Thus, the extraction/dilution section 43 in this embodiment is designed as follows. According to driving of the arm drive section 50, the nozzle 49 is moved above the feces sampling container 1 which is located at the detection position of the container detection sensor 36, and the arm 48 is moved downward to allow the acute-angled lower end of the nozzle 49 to penetrate the sealing film 16 of the feces sampling container 1. Then, the fecal suspension 17a in the feces sampling container 1 is sucked by 10 µL through the nozzle 49. According to further driving of the arm drive section 50, the arm 48 is moved upward from this position, and the support column 47 is rotated to move the nozzle 49 above the cell 42a rotationally moved to a frontward position. Then, after the arm 48 is moved downward, the sucked fecal suspension 17a and 100 µL of diluting solution is discharged into this cell 42a in turn, and the discharged fecal suspension 17a and diluting solution are mixed together.

In this embodiment, a transparent and colorless diluting solution is used. As one example, the diluting solution may be prepared as follows:

| | |
|---|---|
| 30 mM | MES (2-Morpholinoethanesulfonic acid, monohydrate: pH 6.3) |
| 0.9% | sodium chloride |
| 0.2% | bovine serum albumin |
| 0.2% | boric acid |
| 1.8% | polyethylene glycol 20,000 |
| 0.1% | sodium azide |

As shown in FIGS. 6 and 8, the reagent addition section 51 comprises a manipulation section 52 disposed on the left side of the rotary table 40, a pump section 53 in fluid communication with the manipulation section 52, and a reagent mounting section 54 capable of mounting a reagent bottle B thereon. The manipulation section 52 includes a support column 55 extends upward from the base 31, an arm 56 attached to the support column 55 in a cantilevered manner to extend in a direction orthogonal to the support column 55, a nozzle 57 and a stirring bar 58 which are attached to the end of the arm 56 to extend downward, and an arm drive section 59 operable to stretch and retract the support column 55 relative to the base 31 in a direction indicated by the arrow Y6 and rotate the support column 55 around its axis in a direction indicated by the arrow Y7. The pump portion 53 is designed to allow the nozzle 57 to suck a predetermined amount of reagent 60 from the reagent bottle B, and internally provided with a syringe (not shown) capable of being stroke-controlled by a ball screw or the like to discharge the sucked reagent 60 from the nozzle 57. This syringe is in fluid communication with the nozzle 57 through connection tube T3.

Thus, the reagent addition section 51 in this embodiment is designed as follows. According to driving of the arm drive section 59, the nozzle 57 is moved above the reagent bottle B, and the arm 56 is moved downward. Then, the reagent 60 in the reagent bottle B is sucked by 50 μL through the nozzle 57. According to further driving of the arm drive section 59, the arm 56 is moved upward from this position, and the support column 55 is rotated to move the nozzle 57 above the cell 42a located at a specific position. Then, the arm 56 is moved downward, and the reagent 60 of 50 μL is discharged into this cell 42a. Further, the stirring bar 58 is inserted into the cell 42a added with the reagent 60, and rotated to stir the reagent 60 in the cell 42a. The reagent addition section 51 is designed to add the reagent into the cell 42 which is rotationally moved to a rightward position relative to the position where the diluting solution and others are added to the cell 42a by the extraction/dilution section 43.

The reagent 60 includes a gold colloid-labeled antihuman hemoglobin antigen. When a diluted fecal suspension 17a is mixed with the reagent 60, gold colloid particles of this antigen will be aggregated to cause color change (from red-violet to gray). Specifically, as one example of this reagent 60, the following reagent is known:

| | |
|---|---|
| 130 μL/mL | gold colloid-labeled antihuman hemoglobin antigen (rabbit) (maximum absorption wavelength: 540 nm) |
| 5 mmol/L | TES (N-Tris(hydroxymethyl)methyl-2-aminoethanesulfolic acid) |
| 0.1% | bovine serum albumin |
| 3% | mannitol |
| 0.025% | xanthurenic acid |
| 0.05% | EDTA (Ethylenediamminetetraacetic acid) 2Na Cu |
| 0.05% | sodium azide |

The optical-absorbance measurement section 61 has a well-known structure employed in spectrophotometers and others, and its detailed description will be omitted herein. Briefly, the optical-absorbance measurement section 61 is designed to emit light with an appropriately selected wavelength from a light source, such as tungsten lamp, to the cell 42a, and detect light transmitted through the cell 42 by a detector, such as a photodiode, so as to measure light intensities before and after transmission to calculate an optical absorbance in accordance with these intensities. In this embodiment, the optical-absorbance measurement section 61 is located on the base 31 to measure the optical absorbance of the cell 42a which is rotationally moved to a rightward position by the table drive section 42.

The cell cleaning section 62 comprises five cleaning nozzles (not shown) disposed above the rotary table 40 and on the frontward side of the optical-absorbance measurement section 61. The cell cleaning section 62 is operable, after the optical-absorbance measurement, to suck the fecal suspension 17a and others from the cell 42a by the cleaning nozzles, and discharge the cell 42a to a disposal vessel (not shown). The cell cleaning section 62 is also operable to repeatedly suck a given cleaning liquid and discharge it to the cells 42a so as to simultaneously clean the five cells 52a on a cuvette 42a by cuvette 42a basis.

As shown in FIG. 6, the control box 63 is a box-shaped unit enclosing an after-mentioned control device (determinator) 66. The control box 63 is provided with an input section 64 having a start keypad and ten-key keypads, and a printer section 65 for outputting an assay result, on the front surface thereof.

Figure 9:
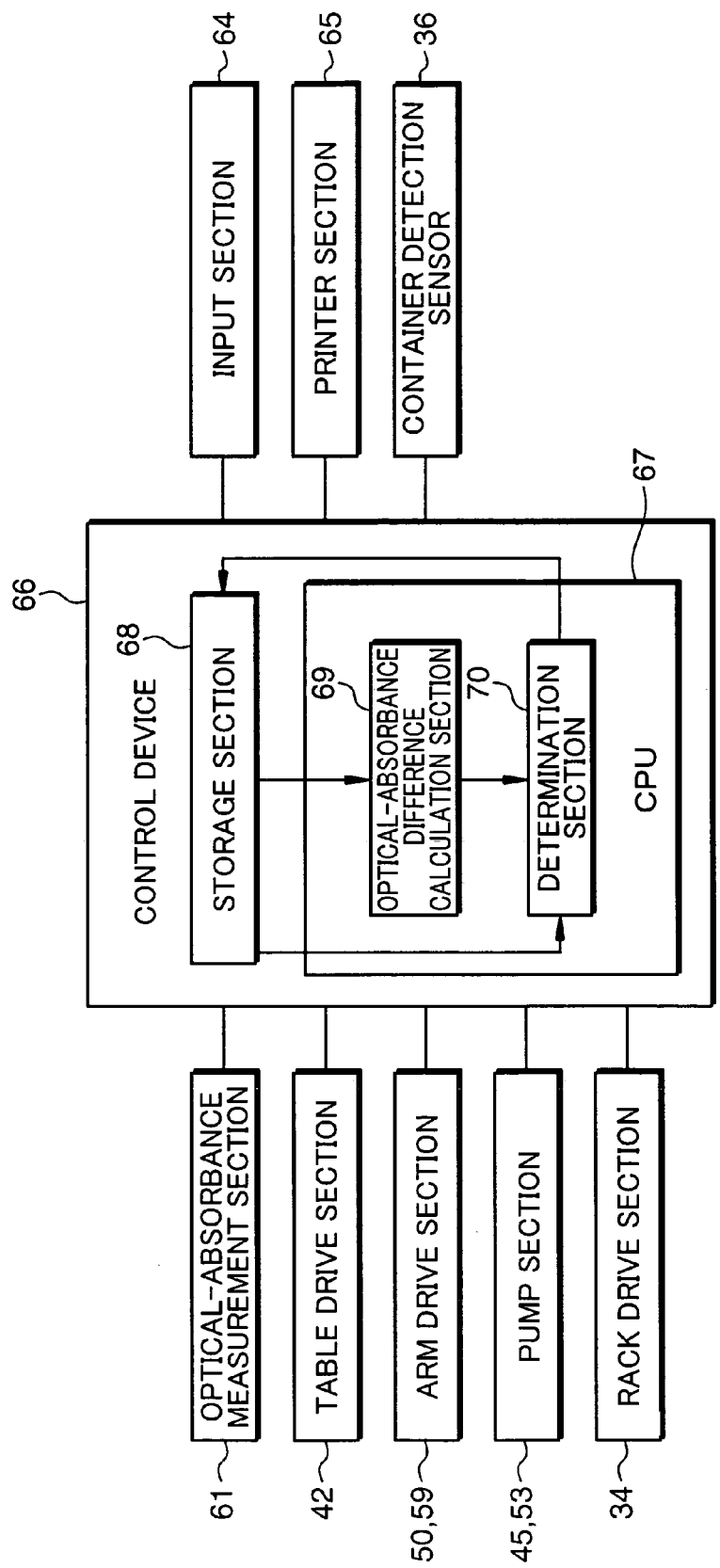
FIG. 9 is a block diagram showing a control unit of the analyzer in FIG. 6.

As shown in FIG. 9, the control device 66 comprises a CPU 67 for performing various processings, and a storage section 68 composed of a RAM, ROM or the like which stores an operation program and others. The control device 66 is operable, in response to pushing the start keypad of the input section 64, to drive the optical-absorbance measurement section 61, the table drive section 42, the arm drive sections 50, 59, the pump sections 45, 53 and the rack drive section 34 according to the operation program so as to perform the assay of the specimen, and output an assay result from the printer section 65. Further, the control device 66 is operable, in response to a detection signal of the container detection sensor 36, to controllably switch between the drive and stop of the rack drive section 34.

Figure 10:
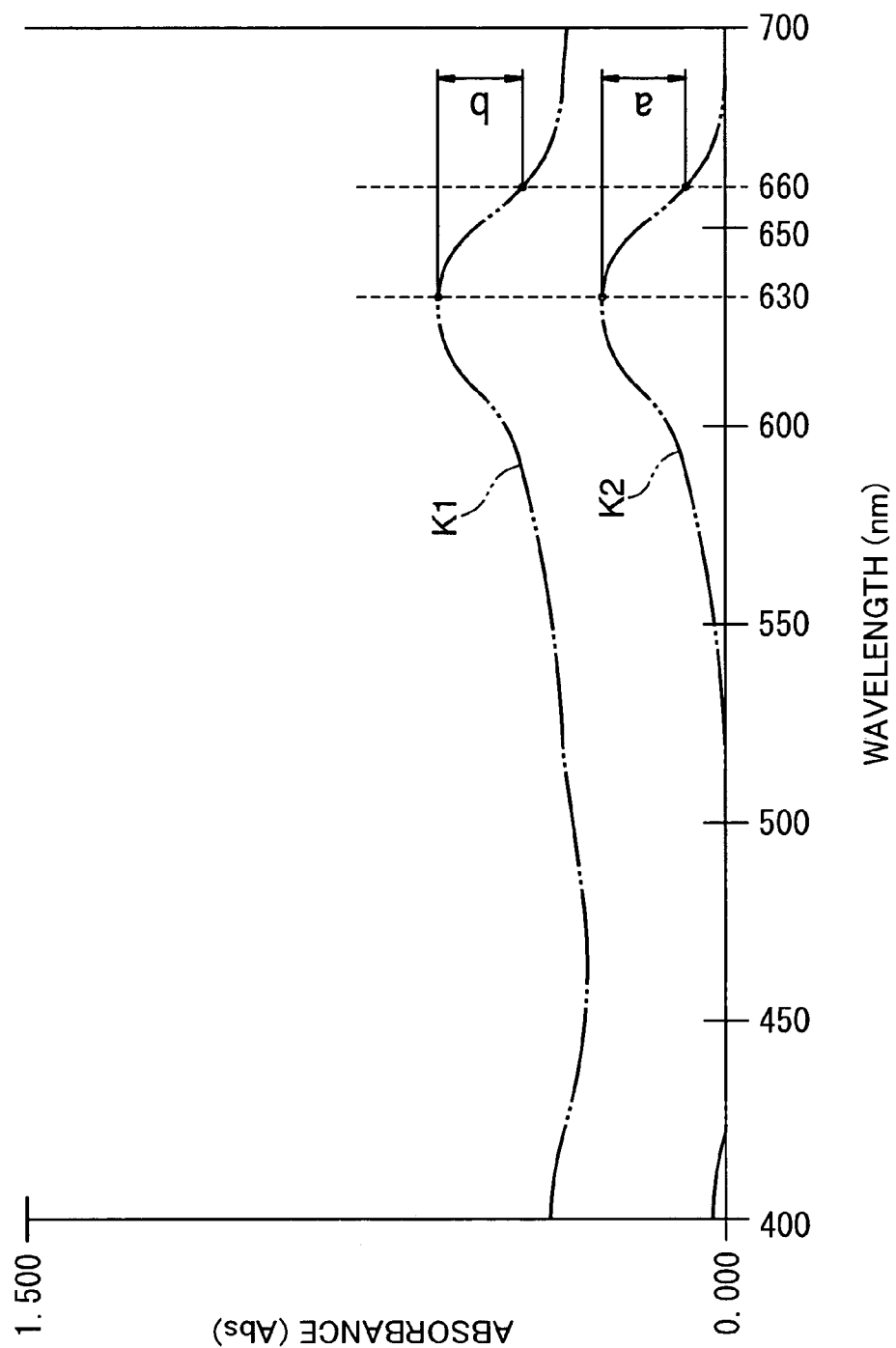
FIG. 10 is a chart showing an optical-absorbance curve of a pigment included in the feces-dissolving liquid, which is measured by the analyzer in FIG. 6.
Figure 12:
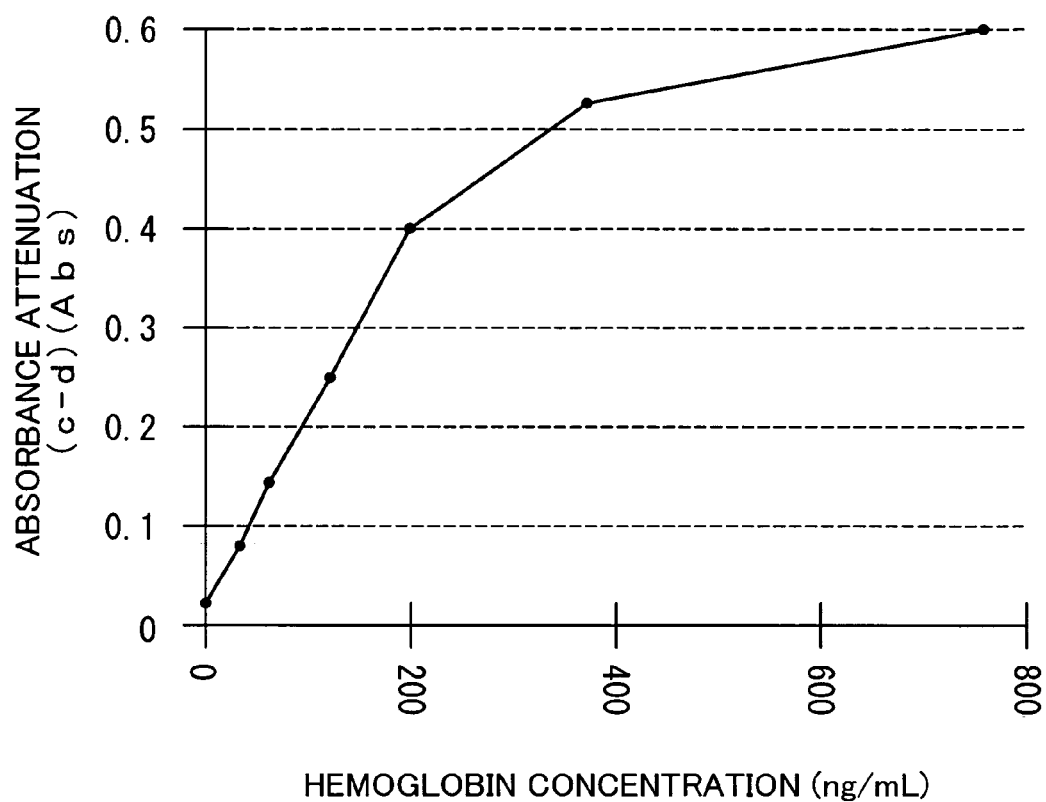
FIG. 12 is a chart showing an analytical curve stored in the analyzer in FIG. 6.

The storage section 68 stores the difference "a" between respective optical absorbance of a pigment (BRILLIANT BLUE FCF) included in a feces-dissolving liquid 17 diluted at a predetermined dilution rate (or a mixture of the feces-dissolving liquid 17 of 10 μL and the diluting solution of 100 μL) at two wavelengths of 630 nm and 660 nm, as shown in FIGS. 10 and 11 (difference "a" will hereinafter be referred to as "reference optical-absorbance difference"), and an analytical curve representing a hemoglobin concentration defined by the attenuation value of the optical absorbance difference of the reagent 60 between 1 minute and 7 minutes from the reaction between the reagent 60 and hemoglobin in the fecal suspension 17a, as shown in FIG. 12.

As shown in FIG. 9, the CPU 67 primarily serves as an optical-absorbance difference calculation section 69 operable to calculate the difference between respective optical absorbance values measured at two wavelengths of 540 nm (maximum absorption wavelength of gold colloid particles) and 660 nm (wavelength having a relatively low absorption to gold colloid particles), and a determination section 70 operable to perform a subtraction of a first difference between respective optical-absorbance values measured at the two wavelengths after 1 minute from the reaction between the reagent 60 and hemoglobin in the fecal suspension 17a (optical-absorbance difference "c" in FIG. 13), and a second difference between respective optical-absorbance values measured at the two wavelengths after 7 minute from the reaction (optical-absorbance difference "d" in FIG. 13) to calculate an optical-absorbance attenuation value (c–d), and-determine the amount (concentration) of hemoglobin in accordance with the attenuation value and the above analytical curve (see FIG. 12).

In this embodiment, the optical-absorbance difference calculation section 69 is also operable to calculate a first difference (optical-absorbance difference "b" in FIG. 12) between respective optical-absorbance values measured at two wavelengths of 630 nm (maximum absorption wavelength of BRILLIANT BLUE FCF) and 660 nm (wavelength having a relatively low absorption to BRILLIANT BLUE FCF), and the determination section 70 is operable to determine whether the optical-absorbance difference "b" falls within ±10% of the above reference optical absorbance difference "a" (see FIGS. 10 and 11) so as to determine the adequacy of the amount of the fecal suspension 17a extracted and supplied to the cell 42a by the extraction/dilution section 43.

Figure 14:
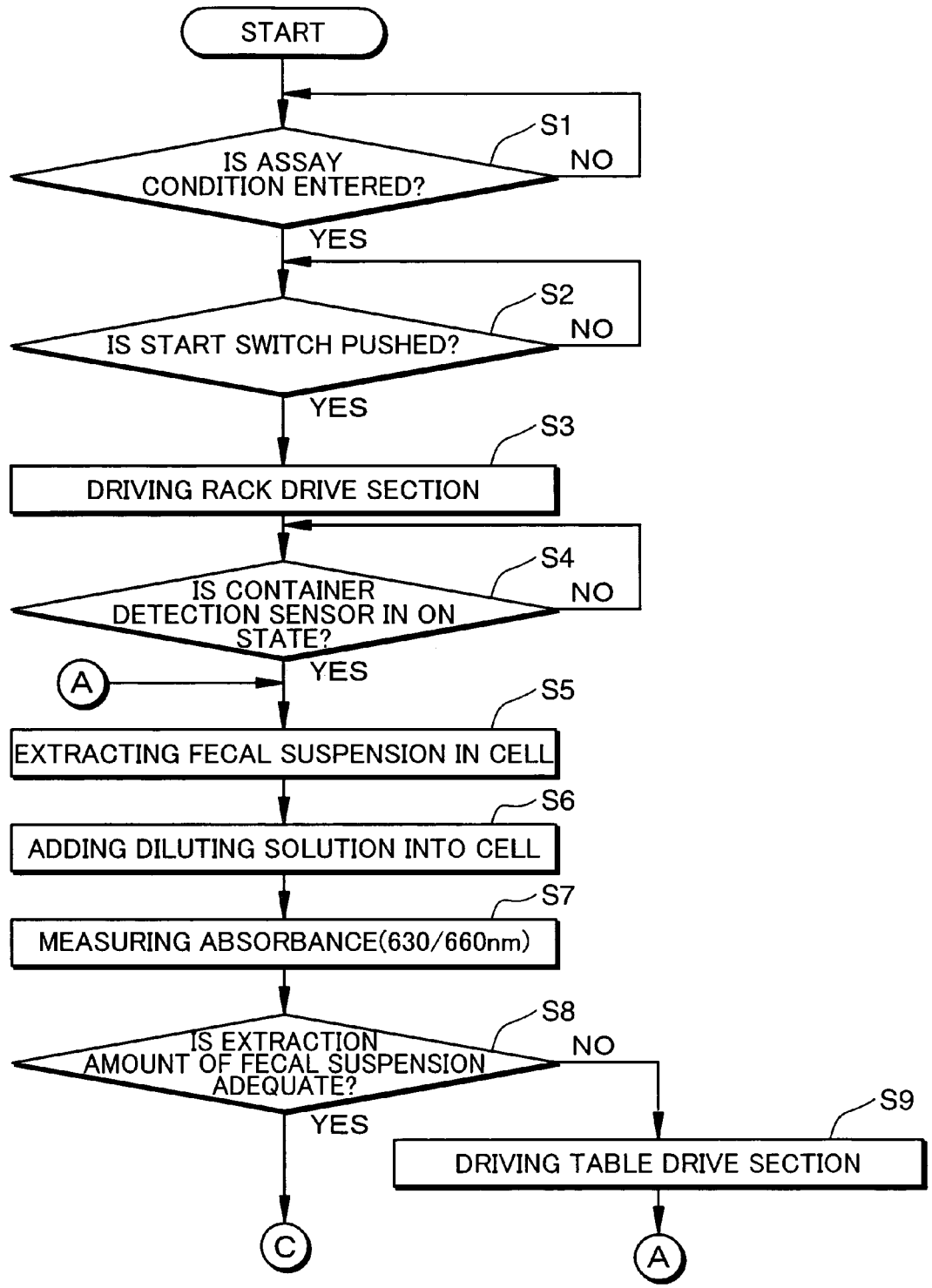
FIG. 14 is a flowchart showing a processing according to the control unit in FIG. 9.

With reference to the top plan view in FIG. 6 and the flowcharts in FIGS. 14 and 15, a processing performed by the control device 66 will be described below.

As an operation before an assay, a user places a container rack 35 holding the feces sampling container 1, on the container holder 32, and places the reagent bottle B containing the reagent 60, on the reagent mounting section 54. Then, when the processing of the control device 66 starts up, it is determined whether an assay condition (e.g. a lot number of the reagent 60) is entered from the input section 64 (Step S1). If it is determined that no assay condition is entered (NO in Step S1), Step 1 will be repeated. When it is determined that an assay condition is entered (YES in Step S1), it is determined whether the start keypad of the input section 64 is pushed (Step S2).

If it is determined that the start keypad is not pushed (NO in Step S2), Step S2 will be repeated. When it is determined that the start keypad is pushed (YES in Step S2), the rack drive section 34 is driven (Step S3) to transfer the container rack 35. Then, it is determined whether the container rack 35 is detected by the container detection sensor 36 (Step S4). If it is determined that the container rack 35 is not detected (NO in Step S4), Step S4 will be repeated. When it is determined that the container rack 35 is detected (YES in Step S4), the extraction/dilution section 43 extracts the fecal suspension 17a from the feces sampling container 1 into the cell 42a in an amount of 2 mL (Step S5: extraction step), and adds and mixes the diluting solution into/with this cell 42a in an amount of 2 mL (Step S6: mixing step).

Then, the table drive section 42 is driven to move the cell 42a containing the fecal suspension 17a to a rotational position corresponding to the optical-absorbance measurement section 61. Further, the optical absorbance of the diluted fecal suspension 17a is measured at the two wavelengths of 630 nm and 660 nm, as shown in FIG. 10 (Step S7: detection step) to calculate the difference "b" between these optical-absorbance values, and this optical-absorbance difference "b" is compared with the difference "a" between respective optical-absorbance values measured at the two wavelengths in the feces-dissolving liquid 17 diluted at a predetermined dilution rate so as to determine the adequacy of the amount of the extracted fecal suspension 17a (Step S8: determination step). Specifically, as the concentration of feces is increased, an optical-absorbance curve K1 of the mixture of the fecal suspension 17a (10 μL) and the diluting solution (100 μL) is shifted to a position causing increase in optical absorbance, relative to an optical-absorbance curve K2 of a mixture of the feces-dissolving liquid 17 (10 μL) and the diluting solution (100 μL). Thus, the peak height "b" (the difference between respective optical absorbance values at 630 nm and 660 nm) of the optical-absorbance curve K1 can be compared with the peak height (reference optical-absorbance difference) "a" of the optical-absorbance curve K2 to determine the adequacy of the concentration of BRILLIANT BLUE FCF while eliminating an error due to the concentration of feces. In this embodiment, the amount of the extracted fecal suspension 17a is determined to be adequate when the optical-absorbance difference "b" falls within ±10% of the optical-absorbance difference "a", as shown in FIG. 11.

In the above Step S8, if it is determined that the extraction amount of the fecal suspension 17a is inadequate (NO in Step S8), after driving the table drive section 42 to move a different one of the cells 42a to a position corresponding to the extraction/dilution section 43 (Step S9), Step S5 will be repeated (or an re-assay will be performed with respect to the same fecal suspension 17a). When it is determined that the extraction amount of the fecal suspension 17a is adequate (YES in Step S8), the table drive section 42 is driven to move the cell 42a to a rotational position corresponding to the reagent addition section 51. Then, the reagent 60 is added into this cell 42a in an amount of 50 μL through the nozzle 57 of the reagent addition section 51, and the obtained mixture is stirred by the stirring bar 58 (Step S10).

Figure 13:
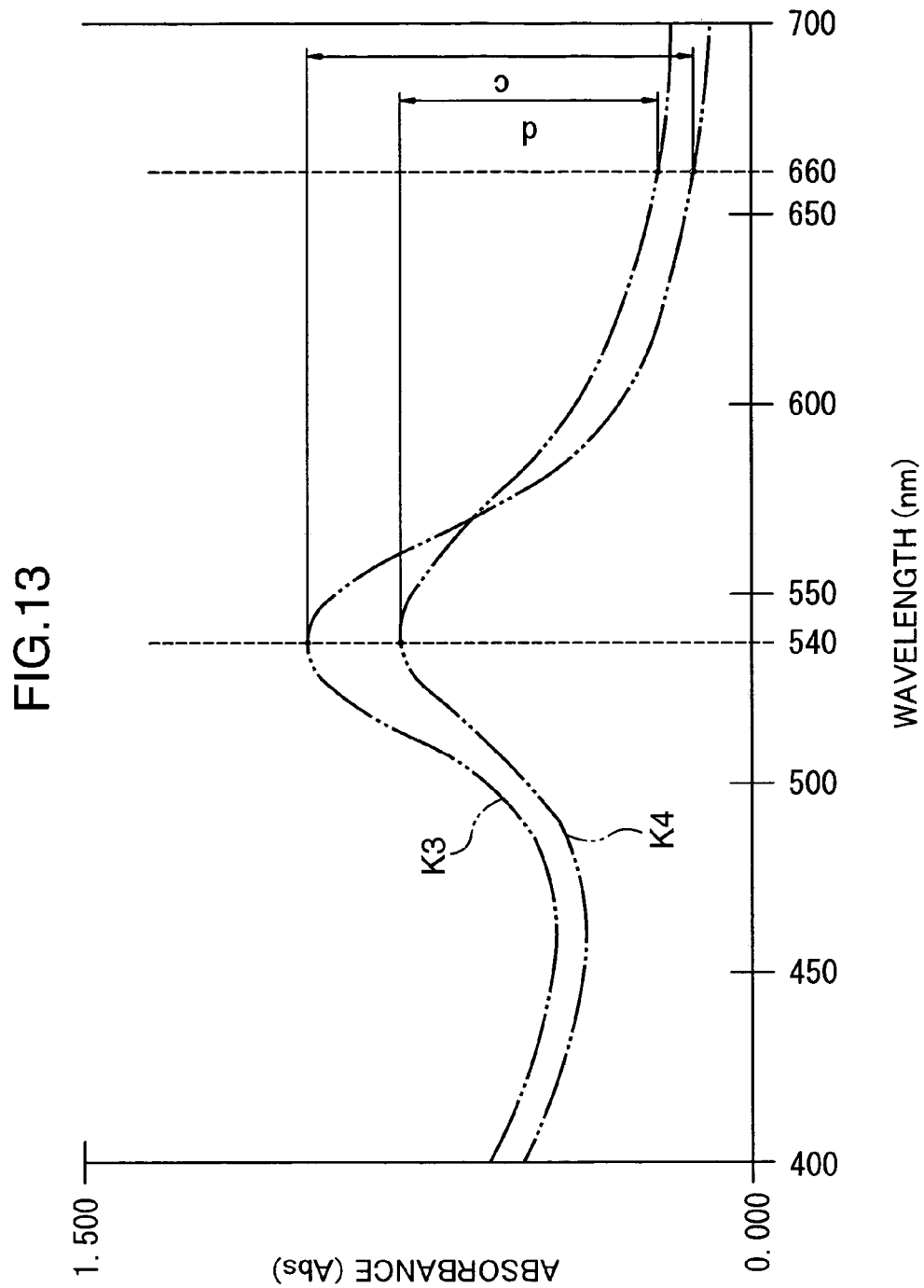
FIG. 13 is a chart showing an optical-absorbance curve of hemoglobin included in the fecal suspension, which is measured by the analyzer in FIG. 6.

Then, the table drive section 42 is driven to rotate the cell 42a to the side of the optical-absorbance measurement section 61. Then, respective absorbance values of the mixture of the fecal suspension 17a and the reagent 60 at the two wavelengths of 540 nm and 660 nm and at each time point after 1 minute and 7 minutes from the reaction between the reagent 60 and hemoglobin in the diluted fecal suspension 17a (Step S11). Further, the concentration of hemoglobin is quantitatively determined in accordance with these optical absorbance values and the analytical curve in FIG. 12, and the determined value is stored on the storage device 68 (Step S12). Specifically, as described above, the gold colloid particles of the reagent 60 have a property of changing color in response-to the progress of the reaction with hemoglobin. Thus, as shown in FIG. 13, the peak height (the difference between respective optical-absorbance valued measured at 540 nm and 660 nm) "d" of the optical-absorbance curve K4 after 7 minutes after the reaction becomes lower than the peak height "c" of the optical-absorbance curve K3 after 1 minute after reaction. Therefore, the value of optical absorbance attenuated between 1 minute and 7 minutes after the reaction can be determined by performing a subtraction of the optical-absorbance difference "c" and the optical-absorbance difference "d", and a hemoglobin concentration corresponding to this attenuation value can be derived from the analytic curve in FIG. 12. For example, when the attenuation value is 0.4 Abs, the hemoglobin concentration can be derived as about 200 ng/mL.

After the quantitative determination of the hemoglobin concentration, the rack drive section 34 is driven to transfer the container rack 35 to the discharge section 33b (Step S13), and it is determined whether the container detection sensor 36 is in ON state (Step S14). If it is determined that the container detection sensor 36 is in ON state (YES in Step S14), the table drive section 42 will be driven to move a different one of the cells 42a to a position corresponding to the extraction/dilution section 43 (Step S15) so as to repeat Step S5 (or to enter a new assay operation for the fecal suspension 17a as a next analyte to be assayed).

When it is determined that the container detection sensor 36 is in OFF state (NO in Step S14), it is determined whether a given time has lapsed from initiation of the detection of the container detection sensor 36 (Step S16). If it is determined that the given time has not lapsed (NO in Step S16), Step S14 will be repeatedly performed. When it is determined that the given time has lapsed (YES in Step S16), the quantitative value stored on the storage section 68 is output from the printer section 66 (Step S17), and this processing is completed.

As mentioned above, according to the feces sampling container 1, the feces-dissolving liquid 17 is colored a different color from that of the diluting solution. Thus, the adequacy of the extraction amount of the extracted fecal suspension 17a can be determined by detecting a pigment concentration of the feces-dissolving liquid 17 included in the mixture of the extracted fecal suspension 17a and the diluting solution of 100 µL. Specifically, when the fecal suspension 17a is mixed with the diluting solution of 100 µL in an amount of less than 10 µL, the concentration of a pigment included in this mixture is less than the concentration of a pigment to be included in a mixture of the feces-dissolving liquid 17 of 10 µL and the diluting solution of 100 µL. Therefore, the deficiency in amount of the extracted fecal suspension 17a can be determined by the comparison between these concentrations, Thus, according to the feces sampling container 1, the concentration of a pigment to be included in the feces-dissolving liquid 17 diluted in a proper dilution rate can be compared with the concentration of a pigment included in the mixture of the extracted fecal suspension 17a and the diluting solution of 100 µL to determine whether the amount of the extracted fecal suspension 17a is adequate.

Further, according to the assay method employed in the aforementioned inspection apparatus 30, a diluting solution having a different concentration (0: transparent) from that of the feces-dissolving liquid 17 with respect to a specific pigment (BRILLIANT BLUE FCF) is added in an amount of 100 µL, and then the concentration of the specific pigment included in the obtained mixture is be detected. Then, based on the detected pigment concentration, the adequacy of the extraction amount of the fecal suspension 17a can be determined. Specifically, when the fecal suspension 17a is mixed with the diluting solution of 100 µL in an amount of less than 10 µL, the concentration of the specific pigment included in this mixture is less than the concentration of the specific pigment to be included in a mixture of the feces-dissolving liquid of 10 µL and the diluting solution of 100 µL. Therefore, the deficiency in amount of the extracted fecal suspension 17a can be determined by the comparison between these concentrations, Thus, according to the above assay method, the concentration of the specific pigment to be included in the feces-dissolving liquid 17 diluted in a proper dilution rate can be compared with the concentration of the specific pigment included in the mixture of the extracted fecal suspension 17a and the diluting solution of a given amount to determine whether the amount of the extracted fecal suspension 17a is adequate.

FIG. 11 shows test data for checking accuracy in determining the extraction amount of the fecal suspension 17a according to the above assay method. When the fecal suspension 17a is accurately extracted in an amount of 10 µL as in Data 1, the optical-absorbance difference was 0.116, and a determination of "adequate" could be obtained. When only the diluting solution is assayed as in Data 2, the optical-absorbance difference was 0.000, and a determination of "inadequate" could be obtained. When the fecal suspension 17a is extracted in an amount of 5 µL, which is one-half of a proper amount, as in Data 3, the optical-absorbance difference was 0.060, and a determination of "inadequate" could be obtained. While the criterion for the determination of "adequate" in the above embodiment has been defined as "10±% of the reference optical-absorbance difference "a"", it may be appropriately set within a range allowing the concentration of hemoglobin to be determined quantitatively and accurately.

In the above assay method, an optical absorbance is measured at two wavelengths of a primary wavelength of 630 nm and an auxiliary wavelength of 660 nm. Thus, the extraction amount of the fecal suspension 17a can be accurately determined regardless of the concentration of feces in the fecal suspension 17a. More specifically, if the optical absorbance is measured only at a maximum absorption wavelength (630 nm) of the specific pigment (BRILLIANT BLUE FCF), the measured optical-absorbance value will be varied depending on the concentration of feces (pigment residing in feces) included in the fecal suspension 17a, or the optical-absorbance curve K2 obtained from the feces-dissolving liquid 17 will be sifted in a direction causing increase in optical absorbance as the concentration of feces is increased. Thus, even if this optical-absorbance value is compared with an optical-absorbance value at the maximum absorption wavelength (630 nm) of the feces-dissolving liquid 17 diluted in a predetermined dilution rate, the difference between these values will include an error depending on the pigment residing in the feces. In contrast, in the above assay method, the optical absorbance is measured at each of two wavelengths of the maximum absorption wavelength (630 nm) of the specific pigment and the auxiliary wavelength (660 nm) having relatively low absorption to the specific pigment. Thus, the optical-absorbance difference between two points on an optical-absorbance curve obtained from the mixture of the extracted fecal suspension 17a and the diluting solution of 100 µL (i.e. the peak height of the optical-absorbance curve K obtained from this mixture with respect to the specific pigment) can be compared with the optical-absorbance difference between two points on the optical-absorbance curve obtained from a mixture of the feces-dissolving liquid of 10 µL and the diluting solution of 100 µL (i.e. the peak height of the optical-absorbance curve K2 obtained from this mixture with respect to the specific pigment). That is, the peak heights of the two optical-absorbance curves K1, K2 can be compared with one another to accurately determine the adequacy of the extraction amount of the fecal suspension 17a while eliminating an error due to the concentration of feces.

An advantageous embodiment of the invention has been shown and described. It is obvious to those skilled in the art that various changes and modifications may be made therein without departing from the spirit and scope thereof as set forth in appended claims. For example, while the above assay method comprises coloring a feces-dissolving liquid 17, and measuring the optical absorbance of a mixture of the feces-dissolving liquid 17 and a transparent and colorless diluting solution to determine the adequacy of the extraction amount of the feces-dissolving liquid 17, the optical absorbance of a mixture of a transparent and colorless feces-dissolving liquid 17 and a colored diluting solution may be measured to determine the adequacy of the extraction amount of the feces-dissolving liquid 17. Alternatively, the adequacy of the extraction amount of the feces-dissolving liquid 17 may also be determined by measuring the optical absorbance of a pigment included in either one of the diluting solution and the feces-dissolving liquid 17.

When the diluting solution is colored, a pigment having a different maximum absorption wavelength from that of a color of the feces-dissolving liquid 17 may be selected. For example, a usable pigment other than the above BRILLIANT BLUE FCF may be a pigment having an absorption maximum in the range of 400 to 800 nm, such as indigocarmine, amaranth, erythrosine, new coccine, methylene blue or inorganic pigment. These pigments may also be used for coloring the feces-dissolving liquid 17.

While the measurement of optical absorbance in the above embodiment has been made at two wavelengths of a primary wavelength of 630 nm and an auxiliary wavelength of 660 nm, these wavelengths may be appropriately selected depending on a color of the feces-dissolving liquid 17 or diluting solution.

In addition, according to the above analyzer 30, a conventional analyzer having an optical-absorbance measurement section 61 for quantitatively determining a hemoglobin concentration may be used in combination with some modification of an operation program or the like to achieve both functions of determining the adequacy of the amount of the extracted fecal suspension 17a and quantitatively determining a hemoglobin concentration in the fecal suspension 17a.

While the above embodiment has been described by taking the analyzer 30 for quantitatively determining a hemoglobin concentration, an analyte is not limited to hemoglobin, but may be any other component included in feces, such as bilirubin, urobilin or *Helicobacter pylori* antigen.

Further, even if the fecal suspension 17a is extracted using a nozzle 49 as in the analyzer 30, and the clogging of the nozzle 49 occurs, the adequacy of the extraction amount of the fecal suspension 17a can be determined by optical-absorbance measurement section 61 and the control device 66.

While the assay method employed in the analyzer 30 has been described in connection with the case where each of the pigment of the feces-dissolving liquid 17 and the gold collide particles has a different maximum absorption wavelength, it is not essential to have different maximum absorption wavelengths. That is, even if each of the pigment of the feces-dissolving liquid 17 or diluting solution and the gold collide particles has the same maximum absorption wavelength, the adequacy of the extraction amount of the fecal suspension 17a can be determined by comparing the reference optical-absorbance difference "a" for the feces-dissolving liquid 17 and the optical-absorbance difference "b" for the extracted fecal suspension 17a, and the quantitative determination of hemoglobin can be performed by calculating an attenuation value between 1 minute and 7 minutes after the reaction between hemoglobin and the reagent 60. More specifically, when either one or both of the feces-dissolving liquid 17 and the diluting solution are colored, each color of at least the feces-dissolving liquid 17 and the diluting solution may be selected to have a different in absorption wavelength. Further, when the feces-dissolving liquid 17 and the diluting solution are colored using the same pigment, each pigment of at least the feces-dissolving liquid 17 and the diluting solution may be adjusted to have a different concentration.

Further, while the diluting solution and the reagent in the above embodiment have been provided separately, the reagent may be included as one component the diluting solution, and the quantity of an analyte may be determined immediately after determining the adequacy of the extraction amount of the fecal suspension 17a.

Furthermore, while a pigment concentration in the above embodiment has been determined based on the measurement of optical absorbance, it may be determined using the transmittance of the diluted fecal suspension 17a. Alternatively, a light-emitting material capable of emit light in response to light having a particular wavelength may be added to the feces-dissolving liquid 17 in advance, and the amount of the fecal suspension 17a may be determined in accordance with the level of light emission from the diluted fecal suspension 17a irradiated with the above light having the particular wavelength.

As described above, a novel feces sampling container contains a feces-dissolving liquid in such a manner as to be extracted by an analyzer. In this feces sampling container, the feces-dissolving liquid is colored a different color from that of a diluting solution to be added into an fecal suspension formed by dispersing feces in the feces-dissolving liquid and extracted by the analyzer, whereby the adequacy of the extraction amount of the fecal suspension can be determined by detecting the pigment concentration of the feces-dissolving liquid to be changed in response to adding the diluting solution into the fecal suspension in a predetermined amount.

Also, a novel method is adapted to assay a fecal suspension which is formed by dissolving feces in a feces-dissolving liquid contained in a feces sampling container, and extracted from the feces sampling container. This assay method comprises: an extraction step of extracting the fecal suspension; a mixing step of adding and mixing a diluting solution having a different concentration from that of the feces-dissolving liquid with respect to a specific pigment, into/with the extracted fecal suspension in a predetermined amount; a detection step of detecting the concentration of the specific pigment to be changed in response to the mixing of the diluting solution; and a determination step of determining the adequacy of the extraction amount of the fecal suspension in accordance with the detected concentration of the specific pigment.

The diluting solution herein means a solution for diluting the fecal suspension, but it does not mean a solution for diluting the specific pigment. Thus, the specific pigment of the diluting solution may have a concentration, greater than that of the specific pigment in the feces-dissolving liquid.

In a first preferred embodiment of the above assay method, the specific pigment in either one of the feces-dissolving liquid and the diluting solution has a concentration of zero.

In a second preferred embodiment of the above assay method, the extraction step includes extracting the fecal suspension into an optical-absorbance measuring vessel; the mixing step includes adding the diluting solution into the vessel; the detection step includes measuring the optical absorbance of the diluted fecal suspension at each of two wavelengths consisting of a first wavelength around a maximum absorption wavelength of the specific pigment and a second wavelength different from the first wavelength; and the determination step includes calculating a first deference between the measure optical-absorbance values, comparing the first difference with a second difference between respective optical-absorbance values measured at the two wavelength in the feces-dissolving liquid diluted at a predetermined dilution rate, and determining the adequacy of the extraction amount of the fecal suspension in accordance with the comparison result.

Further, a novel analyzer comprises: an extractor for extracting from a feces sampling container a fecal suspension which is formed by dispersing feces in a feces-dissolving liquid contained in the feces sampling container; a diluter for adding and mixing a diluting solution having a different concentration from that of the feces-dissolving liquid with respect to a specific pigment, into/with the extracted fecal suspension in a predetermined amount; a detector for detecting the concentration of the specific pigment to be changed in response to the addition of the diluting solution, and a determinator for determining the adequacy of the extraction amount of the fecal suspension in accordance with the detected concentration of the specific pigment.

In a first preferred embodiment of the above analyzer, the specific pigment in either one of the feces-dissolving liquid and the diluting solution has a concentration of zero.

In a seconded preferred embodiment of the above analyzer, the analyzer is designed, when the determinator determines that the extraction amount of the fecal suspension is inadequate, to re-extract the fecal suspension from the feces sampling in which the determined fecal suspension has been contained, to re-add the diluting solution into the re-extracted fecal suspension, to detect the concentration of the specific pigment included in the mixture of the re-extracted fecal suspension and the re-added diluting solution, and to re-determine the adequacy of the extraction amount of the re-extracted fecal suspension in accordance with the re-determination result.

In a third preferred embodiment of the above analyzer, the detector is operable to measure the optical absorbance of the diluted fecal suspension at each of two wavelengths consisting of a first wavelength around a maximum absorption wavelength of the specific, pigment and a second wavelength different from the first wavelength; and the determinator is operable to compare a first difference between respective measure optical-absorbance values measured by the detector with a second difference between respective optical-absorbance values measured at the two wavelength in the feces-dissolving liquid diluted at a predetermined dilution rate, and determine the adequacy of the extraction amount of the fecal suspension in accordance with the comparison result.

In a fourth preferred embodiment of the above analyzer, the analyzer further includes a reagent adder operable to add into the diluted fecal suspension a reagent capable of changing color in response to the reaction with an analyte of the fecal suspension. Further, the detector is operable to measure the optical absorbance of the mixture of the diluted fecal suspension and the added reagent at each of two wavelengths including a maximum absorption wavelength of the color of the reagent before the addition; and the determinator is operable to perform a subtraction of a first difference between respective optical-absorbance values measured after a lapse of a first time-period from the reaction between the analyte and the reagent, and a second difference between respective optical-absorbance values measured after a lapse of a second time-period greater than the first time-period, to calculate an attenuation value in optical absorbance, and determine the quantity of the analyte in accordance with the attenuation value, and an analytical curve of the concentration and optical-absorbance attenuation value of the analyte.

In a fifth preferred embodiment of the above analyzer, the extractor is operable to extract the fecal suspension from the feces sampling container by use of a nozzle.

According to the feces sampling container, the feces-dissolving liquid is colored a different color from that of the diluting solution. Thus, the adequacy of the extraction amount of the fecal suspension can be determined by detecting the pigment concentration of the feces-dissolving liquid included in a mixture of the extracted fecal suspension and the diluting solution added in a predetermined amount. More specifically, if the extraction amount of the fecal suspension is deficient relative to the above predetermined amount of the diluting solution, the concentration of the pigment of the feces-dissolving liquid included in the above mixture will be less than the concentration of the pigment to be included in a mixture of the feces-dissolving liquid extracted in a proper extraction amount and the diluting solution added in the predetermined amount. This means that the deficiency in amount of the extracted fecal suspension can be determined by comparing these concentrations.

As described above, the feces sampling container makes it possible to determine the adequacy of the amount of the extracted fecal suspension by comparing the concentration of the pigment to be included in the feces-dissolving liquid diluted at a proper dilution rate, with the concentration of the pigment included in the mixture of the extracted fecal suspension and the diluting solution added in the predetermined amount.

According to the assay method, a diluting solution having a different concentration from that of the feces-dissolving liquid with respect to a specific pigment is added into the extracted fecal suspension in a predetermined amount, and the concentration of the specific pigment included in this mixture is detected. Then, the adequacy of the extraction amount of the fecal suspension can be determined in accordance with the detected concentration of the specific pigment. More specifically, if the extraction amount of the fecal suspension is deficient relative to the above predetermined amount of the diluting solution, the concentration of the specific pigment included in the above mixture will be less than the concentration of the specific pigment to be included in a mixture of the feces-dissolving liquid extracted in a proper extraction amount and the diluting solution added in the predetermined amount. This means that the deficiency in amount of the extracted fecal suspension can be determined by comparing these concentrations.

As described above, the assay method makes it possible to determine the adequacy of the amount of the extracted fecal suspension by comparing the concentration of the specific pigment to be included in the feces-dissolving liquid diluted at a proper dilution rate, or to be included in the diluting solution mixed with the fecal suspension extracted in a proper extraction amount, with the concentration of the specific pigment included in the mixture of the extracted fecal suspension and the diluting solution added in the predetermined amount.

The specific pigment in either one of the feces-dissolving liquid and the diluting solution may be set to have a concentration of zero (the first preferred embodiment of the assay method). In this case, the specific pigment can added in advance simply into either one of the feces-dissolving liquid and the diluting solution to determine the adequacy of the amount of the extracted fecal suspension.

According to the assay method including the detection step of measuring an optical absorbance at each of the two wavelengths (the second preferred embodiment of the assay method), the extraction amount of the fecal suspension can be accurately determined regardless of the concentration of feces in the fecal suspension. More specifically, if the optical absorbance is measured only at a maximum absorption wavelength of the specific pigment, the measured optical-absorbance value will be varied depending on the concentration of feces (pigment residing in feces) included in the fecal suspension, or an optical-absorbance curve obtained from the feces-dissolving liquid will be sifted in a direction causing increase in optical absorbance as the concentration of feces is increased. Thus, even if this optical-absorbance value is compared with an optical-absorbance value at a wavelength around the maximum absorption wavelength of a mixture of the feces-dissolving liquid extracted in a proper extraction amount and the diluting solution added in the predetermined amount, the difference between these values will include an error depending on pigment residing in the feces. In contrast, in the assay method of the present invention, the optical absorbance is measured at each of two wavelengths consisting of a first wavelength around a maximum absorption wavelength of the specific pigment and a second wavelength other than the first wavelength. Thus, a first difference between respective optical-absorbance values of two points on an optical-absorbance curve obtained from the mixture of the extracted fecal suspension and the diluting solution added in the predetermined amount (i.e. the peak height of an optical-absorbance curve obtained from this mixture with respect to the specific pigment) can be compared with a second difference between respective optical-absorbance values of two points on an optical-absorbance curve obtained from a mixture of the feces-dissolving liquid extracted in a proper extraction amount and the diluting solution added in the predetermined amount (i.e. the peak height of an optical-absorbance curve obtained from this mixture with respect to the specific pigment). That is, the peak heights of the two optical-absorbance curves can be compared with one another to accurately determine the adequacy of the extraction amount of the fecal suspension while eliminating an error to be included in the result of the comparison between the optical absorbance values due to the concentration of feces, as described above.

The term "two wavelengths consisting of a first wavelength around a maximum absorption wavelength and a second wavelength different from the first wavelength" means that two wavelengths including a wavelength around a maximum absorption wavelength of the specific pigment may be appropriately selected. Preferably, a maximum absorption wavelength of the specific pigment and a wavelength having a relatively low absorbance to the specific pigment may be selected as the two wavelengths to provide a significantly increased difference between optical-absorbance values at these wavelengths. This makes it possible to relatively reduce an error in the measurement of optical absorbance due to pigment (e.g. pigment residing in feces) other than that in the feces-dissolving liquid and the diluting solution so as to achieve enhanced determination accuracy.

According to the analyzer, a diluting solution having a different concentration from that of the feces-dissolving liquid with respect to a specific pigment is added into the extracted fecal suspension in a predetermined amount, and the concentration of the specific pigment included in this mixture is detected. Then, the adequacy of the extraction amount of the fecal suspension can be determined in accordance with the detected concentration of the specific pigment. More specifically, if the extraction amount of the fecal suspension is deficient relative to the above predetermined amount of the diluting solution, the concentration of the specific pigment included in the above mixture will be less than the concentration of the specific pigment to be included in a mixture of the feces-dissolving liquid extracted in a proper extraction amount and the diluting solution added in the predetermined amount. This means that the deficiency in amount of the extracted fecal suspension can be determined by comparing these concentrations.

As described above, the analyzer makes it possible to determine the adequacy of the amount of the extracted fecal suspension by comparing the concentration of the specific pigment to be included in the feces-dissolving liquid diluted at a proper dilution rate with the concentration of the specific pigment included in the mixture of the extracted fecal suspension and the diluting solution added in the predetermined amount.

The specific pigment in either one of the feces-dissolving liquid and the diluting solution may be set to have a concentration of zero (the first preferred embodiment of the analyzer). In this case, the specific pigment can added in advance simply into either one of the feces-dissolving liquid and the diluting solution to determine the adequacy of the amount of the extracted fecal suspension.

The analyzer may be designed, when it is determined that the extracted amount of the fecal suspension is not adequate, to perform a re-assay (the second preferred embodiment of the analyzer). In this case, a sample including the fecal suspension extracted in a proper amount can be reliably obtained.

According to the analyzer having the detector operable to measure an optical absorbance at each of the two wavelengths (the third preferred embodiment of the analyzer), the extraction amount of the fecal suspension can be accurately determined regardless of the concentration of feces in the fecal suspension. More specifically, if the optical absorbance is measured only at a maximum absorption wavelength of the specific pigment, the measured optical-absorbance value will be varied depending on the concentration of feces (pigment residing in feces) included in the fecal suspension, or an optical-absorbance curve obtained from the feces-dissolving liquid will be sifted in a direction causing increase in optical absorbance as the concentration of feces is increased. Thus, even if this optical-absorbance value is compared with an optical-absorbance value at a wavelength around the maximum absorption wavelength of a mixture of the feces-dissolving liquid extracted in a proper extraction amount and the diluting solution added in the predetermined amount, the difference between these values will include an error depending on the pigment residing in the feces. In contrast, in the analyzer of the present invention, the optical absorbance is measured at each of two wavelengths consisting of a first wavelength around a maximum absorption wavelength of the specific pigment and a second wavelength other than the first wavelength. Thus, a first difference between respective optical-absorbance values of two points on an optical-absorbance curve obtained from the mixture of the extracted fecal suspension and the diluting solution added in the predetermined amount (i.e. the peak height of an optical-absorbance curve obtained from this mixture with respect to the specific pigment) can be compared with a second difference between respective optical-absorbance values of two points on an optical-absorbance curve obtained from a mixture of the feces-dissolving liquid extracted in a proper extraction amount and the diluting solution added in the predetermined amount (i.e. the peak height of an optical-absorbance curve obtained from this mixture with respect to the specific pigment). That is, the peak heights of the two optical-absorbance curves can be compared with one another to accurately determine the adequacy of the extraction amount of the fecal suspension while eliminating an error to be included in the result of the comparison between the optical absorbance values due to the concentration of feces, as described above.

The term "two wavelengths consisting of a first wavelength around a maximum absorption wavelength and a second wavelength different from the first wavelength" has the same meaning as that described above.

According to the analyzer having the reagent adder (the fourth preferred embodiment of the analyzer), the optical absorbance of the reagent and the fecal suspension is measured, and an analyte, or a component to be analyzed, of the fecal suspension is quantitatively determined in accordance with the measured optical absorbance. Thus, this analyzer may be used in combination with a conventional analyzer having an optical-absorbance measurement device (e.g. an apparatus for measuring a hemoglobin concentration in faces) to achieve both functions of determining the adequacy of the amount of the fecal suspension extracted using a nozzle and determining the quantity of the analyte of the fecal suspension.

Further, in the above analyzer, the extractor may be designed to extract the fecal suspension using a nozzle (the fifth preferred embodiment of the analyzer). In this case, even if the clogging of the nozzle occurs, the adequacy of the extraction amount of the fecal suspension can be determined by the detector and the determinator.

This application is based on patent application No. 2003-423873 filed in Japan, the contents of which are hereby incorporated by references.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. An analyzer comprising:
   an extractor for extracting from a feces sampling container a fecal suspension which is formed by dispersing feces in a feces-dissolving liquid contained in the feces sampling container;
   a diluter for adding and mixing a diluting solution into/with the extracted fecal suspension in a predetermined amount, the diluting solution having a different concentration from that of the feces-dissolving liquid with respect to a specific pigment, the specific pigment in either one of the feces-dissolving liquid and the diluting solution having a concentration of zero;
   a detector for detecting the concentration of the specific pigment to be changed in response to the addition of the diluting solution; and
   a determinator for determining the adequacy of the extraction amount of the fecal suspension in accordance with the detected concentration of the specific pigment, wherein:
   the detector is operable to measure the optical absorbance of the diluted fecal suspension at each of two wavelengths consisting of a first wavelength around a maximum absorption wavelength of the specific pigment and a second wavelength different from the first wavelength; and
   the determinator is operable to compare a first difference between respective optical-absorbance values measured by the detector with a second difference between respective optical-absorbance values measured at the two wavelength in the feces-dissolving liquid diluted at a predetermined dilution rate, and determine the adequacy of the extraction amount of the fecal suspension in accordance with the comparison result.

2. An analyzer comprising:
   an extractor for extracting from a feces sampling container a fecal suspension which is formed by dispersing feces in a feces-dissolving liquid contained in the feces sampling container;
   a diluter for adding and mixing a diluting solution into/with the extracted fecal suspension in a predetermined amount, the diluting solution having a different concentration from that of the feces-dissolving liquid with respect to a specific pigment, the specific pigment in either one of the feces-dissolving liquid and the diluting solution having a concentration of zero;
   a detector for detecting the concentration of the specific pigment to be changed in response to the addition of the diluting solution;
   a determinator for determining the adequacy of the extraction amount of the fecal suspension in accordance with the detected concentration of the specific pigment; and
   a reagent adder operable to add into the diluted fecal suspension a reagent capable of changing color in response to the reaction with an analyte of the fecal suspension, wherein:
   the detector is operable to measure the optical absorbance of the mixture of the diluted fecal suspension and the added reagent at each of two wavelengths including a maximum absorption wavelength of the color of the reagent before the addition; and
   the determinator is operable to perform a subtraction of a first difference between respective optical-absorbance values measured at the two wavelengths after a lapse of a first time-period from the reaction between the analyte and the reagent, and a second difference between respective optical-absorbance values measured at the two wavelengths after a lapse of a second time-period greater than the first time-period, to calculate an attenuation value in optical absorbance, and determine the quantity of the analyte in accordance with the attenuation value, and an analytical curve of the concentration and optical-absorbance attenuation value of the analyte.

3. An analyzer comprising:
   an extractor for extracting from a feces sampling container a fecal suspension which is formed by dispersing feces in a feces-dissolving liquid contained in the feces sampling container;
   a diluter for adding and mixing a diluting solution into/with the extracted fecal suspension in a predetermined amount, the diluting solution having a different concentration from that of the feces-dissolving liquid with respect to a specific pigment, the specific pigment in either one of the feces-dissolving liquid and the diluting solution having a concentration of zero;
   a detector for detecting the concentration of the specific pigment to be changed in response to the addition of the diluting solution; and
   a determinator for determining the adequacy of the extraction amount of the fecal suspension in accordance with the detected concentration of the specific pigment, the analyzer being designed, when the determinator determines that the extraction amount of the fecal suspension is inadequate, to re-extract the fecal suspension from the feces sampling in which the determined fecal suspension has been contained, to re-add the diluting solution into the re-extracted fecal suspension, to detect the concentration of the specific pigment included in the mixture of the re-extracted fecal suspension and the re-added diluting solution, and to re-determine the adequacy of the extraction amount of the re-extracted fecal suspension in accordance with the re-determination result, wherein:
   the detector is operable to measure the optical absorbance of the diluted fecal suspension at each of two wavelengths consisting of a first wavelength around a maximum absorption wavelength of the specific pigment and a second wavelength different from the first wavelength; and
   the determinator is operable to compare a first difference between respective optical-absorbance values measured by the detector with a second difference between respective optical-absorbance values measured at the two wavelength in the feces-dissolving liquid diluted at a predetermined dilution rate, and determine the adequacy of the extraction amount of the fecal suspension in accordance with the comparison result.

4. The analyzer as defined in claim 3, wherein the extractor is designed to extract the fecal suspension from the feces sampling container by use of a nozzle.

5. An analyzer comprising:
an extractor for extracting from a feces sampling container a fecal suspension which is formed by dispersing feces in a feces-dissolving liquid contained in the feces sampling container;
a diluter for adding and mixing a diluting solution into/with the extracted fecal suspension in a predetermined amount, the diluting solution having a different concentration from that of the feces-dissolving liquid with respect to a specific pigment, the specific pigment in either one of the feces-dissolving liquid and the diluting solution having a concentration of zero;
a detector for detecting the concentration of the specific pigment to be changed in response to the addition of the diluting solution;
a determinator for determining the adequacy of the extraction amount of the fecal suspension in accordance with the detected concentration of the specific pigment, the analyzer being designed, when the determinator determines that the extraction amount of the fecal suspension is inadequate, to re-extract the fecal suspension from the feces sampling in which the determined fecal suspension has been contained, to re-add the diluting solution into the re-extracted fecal suspension, to detect the concentration of the specific pigment included in the mixture of the re-extracted fecal suspension and the re-added diluting solution, and to re-determine the adequacy of the extraction amount of the re-extracted fecal suspension in accordance with the re-determination result; and
a reagent adder operable to add into the diluted fecal suspension a reagent capable of changing color in response to the reaction with an analyte of the fecal suspension, wherein:
the detector is operable to measure the optical absorbance of the mixture of the diluted fecal suspension and the added reagent at each of two wavelengths including a maximum absorption wavelength of the color of the reagent before the addition; and
the determinator is operable to perform a subtraction of a first difference between respective optical-absorbance values measured at the two wavelengths after a lapse of a first time-period from the reaction between the analyte and the reagent, and a second difference between respective optical-absorbance values measured at the two wavelengths after a lapse of a second time-period greater than the first time-period, to calculate an attenuation value in optical absorbance, and determine the quantity of the analyte in accordance with the attenuation value, and an analytical curve of the concentration and optical-absorbance attenuation value of the analyte.

6. An analyzer comprising:
an extractor for extracting from a feces sampling container a fecal suspension which is formed by dispersing feces in a feces-dissolving liquid contained in the feces sampling container;
a diluter for adding and mixing a diluting solution into/with the extracted fecal suspension in a predetermined amount, the diluting solution having a different concentration from that of the feces-dissolving liquid with respect to a specific pigment;
a detector for detecting the concentration of the specific pigment to be changed in response to the addition of the diluting solution; and
a determinator for determining the adequacy of the extraction amount of the fecal suspension in accordance with the detected concentration of the specific pigment, wherein:
the detector is operable to measure the optical absorbance of the diluted fecal suspension at each of two wavelengths consisting of a first wavelength around a maximum absorption wavelength of the specific pigment and a second wavelength different from the first wavelength; and
the determinator is operable to compare a first difference between respective optical-absorbance values measured by the detector with a second difference between respective optical-absorbance values measured at the two wavelength in the feces-dissolving liquid diluted at a predetermined dilution rate, and determine the adequacy of the extraction amount of the fecal suspension in accordance with the comparison result.

7. An analyzer comprising:
an extractor for extracting from a feces sampling container a fecal suspension which is formed by dispersing feces in a feces-dissolving liquid contained in the feces sampling container;
a diluter for adding and mixing a diluting solution into/with the extracted fecal suspension in a predetermined amount, the diluting solution having a different concentration from that of the feces-dissolving liquid with respect to a specific pigment;
a detector for detecting the concentration of the specific pigment to be changed in response to the addition of the diluting solution;
a determinator for determining the adequacy of the extraction amount of the fecal suspension in accordance with the detected concentration of the specific pigment; and
a reagent adder operable to add into the diluted fecal suspension a reagent capable of changing color in response to the reaction with an analyte of the fecal suspension, wherein:
the detector is operable to measure the optical absorbance of the mixture of the diluted fecal suspension and the added reagent at each of two wavelengths including a maximum absorption wavelength of the color of the reagent before the addition; and
the determinator is operable to perform a subtraction of a first difference between respective optical-absorbance values measured at the two wavelengths after a lapse of a first time-period from the reaction between the analyte and the reagent, and a second difference between respective optical-absorbance values measured at the two wavelengths after a lapse of a second time-period greater than the first time-period, to calculate an attenuation value in optical absorbance, and determine the quantity of the analyte in accordance with the attenuation value, and an analytical curve of the concentration and optical-absorbance attenuation value of the analyte.

* * * * *